United States Patent [19]

Nixon et al.

[11] Patent Number: 5,026,707

[45] Date of Patent: Jun. 25, 1991

[54] RING-SUBSTITUTED 2-AMINO-1,2,3,4-TETRAHYDRONAPHTHALENES

[75] Inventors: James A. Nixon; Richard P. Pioch; John M. Schaus; Robert D. Titus, all of Indianapolis, Ind.

[73] Assignee: Eli Lilly and Company, Indianapolis, Ind.

[21] Appl. No.: 464,826

[22] Filed: Jan. 16, 1990

Related U.S. Application Data

[63] Continuation of Ser. No. 197,236, May 23, 1988, abandoned.

[51] Int. Cl.$^5$ ............... A61K 31/495; A61K 31/395; C07D 295/02; C07D 243/08
[52] U.S. Cl. ................... 514/255; 514/218; 540/575; 544/336; 544/392; 544/395; 544/403
[58] Field of Search ............... 540/575; 544/336, 392, 544/395, 403; 514/218, 255

[56] References Cited

U.S. PATENT DOCUMENTS 4,368,199 1/1983 Ancher et al. .................. 544/391
4,845,221 7/1989 Stack et al. ..................... 544/295

FOREIGN PATENT DOCUMENTS 8103491 12/1981 PCT Int'l Appl. .

OTHER PUBLICATIONS

Khristova et al. Chem. Abst. 101-222109k (1984).
Schohe et al. Chem. Abst. 109-149105q (1988).
Schohe et al. Chem. Abst. 110-57322a (1989).

Primary Examiner—Cecilia Shen
Attorney, Agent, or Firm—William C. Martens; Leroy Whitaker

[57] ABSTRACT

This invention provides ring-substituted 2-amino-1,2,3,4-tetrahydronaphthalenes which are selective inhibitors of serotonin reuptake.

36 Claims, No Drawings

RING-SUBSTITUTED 2-AMINO-1,2,3,4-TETRAHYDRONAPHTHALENES

BACKGROUND OF THE INVENTION

During the past decade, the relationship between monoamine uptake and a variety of diseases and conditions has been appreciated and investigated. For example, the hydrochloride salt of fluoxetine (dl-N-methyl-3-phenyl-3-[4-(trifluoromethyl)phenoxy]propanamine) is a selective inhibitor of serotonin (5-hydroxytryptamine) reuptake useful for the treatment of depression, and perhaps for the treatment of eating disorders, alcoholism, and other disorders. Similarly, tomoxetine hydrochloride [(−)-N-methyl-3-(2-methylphenoxy)-propanamine hydrochloride] is a selective inhibitor of norepinephrine uptake being investigated clinically for its antidepressant activity. These compounds are among many taught in U.S. Pat. Nos. 4,018,895, 4,194,009, and 4,314,081 as being potent blockers of the uptake of various physiologically active monoamines, including serotonin, norepinephrine and dopamine.

SUMMARY OF THE INVENTION

The present invention provides novel ring-substituted 2-piperazinyl- or 2-homopiperazinyl-1,2,3,4-tetrahydronaphthalenes which are selective inhibitors of serotonin reuptake and which do not have a direct effect on neuronal receptors. These compounds therefore would be expected to produce fewer side effects since they do not effectively block monoamine receptors or inhibit the reuptake of other monoamines.

More specifically, this invention relates to a compound of the formula

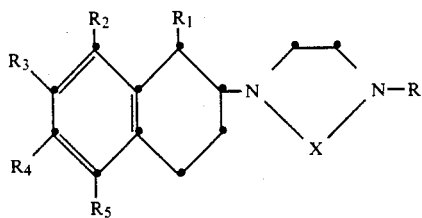

in which
R is hydrogen or methyl; $R_1$ is hydrogen or methyl; X is —CH$_2$CH$_2$— or —CH$_2$CH$_2$CH$_2$—;
$R_2$ is selected from the group consisting of hydrogen, halo, $C_1$-$C_3$ alkoxy, $C_1$-$C_3$ thioalkyl, $C_1$-$C_3$ alkyl, and hydroxy;
$R_3$ is selected from the group consisting of hydrogen and halo;
$R_4$ is selected from the group consisting of hydrogen, halo, $C_1$-$C_3$ alkyl, $C_1$-$C_3$ alkoxy, $C_1$-$C_3$ thioalkyl, and hydroxy;
$R_5$ is selected from the group consisting of hydrogen, halo, $C_1$-$C_3$ alkyl, $C_1$-$C_3$ alkoxy, $C_1$-$C_3$ acyl, fluorosubstituted $C_2$-$C_3$ acyl, fluoro-substituted $C_1$-$C_3$ alkyl, cyano, carboxamide, carboxyl, and $C_1$-$C_3$ hydroxyalkyl; all subject to the following provisos:
(a) if R is methyl, both $R_2$ and R<may be hydrogen;
(b) if $R_1$ is hydrogen, one of $R_2$ and $R_4$ is hydrogen and the other is other than hydrogen;
(c) $R_5$ may be other than hydrogen only when $R_2$ is other than hydrogen; and
(d) $R_3$ may be halo only when $R_4$ is other than hydrogen;

and pharmaceutically acceptable acid addition salts thereof. This invention also provides a pharmaceutical formulation which comprises, in association with a pharmaceutically acceptable carrier, diluent, or excipient, a compound of the formula

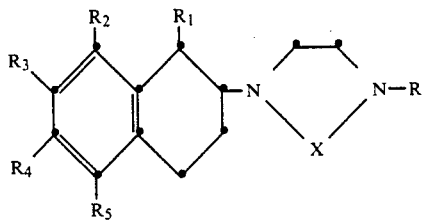

in which
R is hydrogen or methyl; $R_1$ is hydrogen or methyl; X is —CH$_2$CH$_2$— or —CH$_2$CH$_2$CH$_2$—;
$R_2$ is selected from the group consisting of halo, $C_1$-$C_3$ alkoxy, $C_1$-$C_3$ thioalkyl, $C_1$-$C_3$ alkyl, and hydroxy;
$R_3$ is selected from the group consisting of hydrogen and halo;
$R_4$ is selected from the group consisting of hydrogen, halo, $C_1$-$C_3$ alkyl, $C_1$-$C_3$ alkoxy, $C_1$-$C_3$ thioalkyl, and hydroxy;
$R_5$ is selected from the group consisting of hydrogen, halo, $C_1$-$C_3$ alkyl, $C_1$-$C_3$ alkoxy, $C_1$-$C_3$ acyl, fluorosubstituted $C_2$-$C_3$ acyl, fluoro-substituted $C_1$-$C_3$ alkyl, and cyano;
all subject to the following provisos:
(a) if $R_1$ is methyl, both $R_2$ and $R_4$ may be hydrogen;
(b) if $R_1$ is hydrogen, one of $R_2$ and $R_4$ is hydrogen and the other is other than hydrogen;
(c) $R_5$ may be other than hydrogen only when $R_2$ is other than hydrogen; and
(d) $R_3$ may be halo only when $R_4$ is other than hydrogen;

and pharmaceutically acceptable acid addition salts thereof.

A further embodiment of the invention is a method for selectively inhibiting the reuptake of serotonin. More particularly, further embodiments are methods for treating a variety of disorders which have been linked to decreased neurotransmission of serotonin in mammals. Included among these disorders are eating disorders, including obesity, anorexia nervosa, and bulemia, depression, alcoholism, pain, loss of memory, anxiety, smoking, Type II diabetes, obsessive-compulsive behavior, and the like. Any of these methods employ a compound of the formula

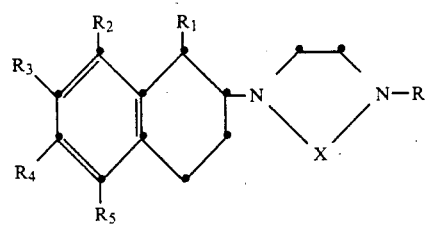

in which
R is hydrogen or methyl; $R_1$ is hydrogen or methyl; X is —CH$_2$CH$_2$— or —CH$_2$CH$_2$CH$_2$—;
$R_2$ is selected from the group consisting of hydrogen, halo, $C_1$-$C_3$ alkoxy, $C_1$-$C_3$ thioalkyl, $C_1$-$C_3$ alkyl, and hydroxy;

$R_3$ is selected from the group consisting of hydrogen and halo;

$R_4$ is selected from the group consisting of hydrogen, halo, $C_1$-$C_3$ alkyl, $C_1$-$C_3$ alkoxy, $C_1$-$C_3$ thioalkyl, and hydroxy;

$R_5$ is selected from the group consisting of hydrogen, halo, $C_1$-$C_3$ alkyl, $C_1$-$C_3$ alkoxy, $C_1$-$C_3$ acyl, fluorosubstituted $C_2$-$C_3$ acyl, fluoro-substituted $C_1$-$C_3$ alkyl, and cyano;

all subject to the following provisos:
(a) if $R_1$ is methyl, both $R_2$ and $R_4$ may be hydrogen;
(b) if $R_1$ is hydrogen, one of $R_2$ and $R_4$ is hydrogen and the other is other than hydrogen;
(c) $R_3$ may be other than hydrogen only when $R_2$ is other than hydrogen; and
(d) $R_3$ may be halo only when $R_4$ is other than hydrogen;

and pharmaceutically acceptable acid addition salts thereof.

DETAILED DESCRIPTION OF THE INVENTION

In the above formula, the term "$C_1$-$C_3$ alkyl" means a straight or branched alkyl chain bearing from one to three carbon atoms. Such $C_1$-$C_3$ alkyl groups are methyl, ethyl, n-propyl, and isopropyl.

The term "$C_1$-$C_3$ alkoxy" means any of methoxy, ethoxy, n-propoxy, and isopropoxy.

The term "halo" means any of fluoro, chloro, bromo, and iodo.

The term "$C_1$-$C_3$ acyl" means any of formyl, acetyl, and propionyl.

The term "fluoro-substituted $C_2$-$C_3$ acyl" means mono-, di-, or tri-fluoro-substituted acetyl, or mono-, di-, tri-, tetra-, or penta-fluoro-substituted propionyl. Specific examples are fluoroacetyl, trifluoroacetyl, $\beta,\beta,\beta$-trifluoropropionyl, $\beta$-fluoropropionyl, $\beta,\beta$-difluoropropionyl, and the like.

The term "fluoro-substituted $C_1$-$C_3$ alkyl" means methyl, mono-, di-, or tri-, or ethyl, mono-, di-, tri-, tetra-, or penta-, or n-propyl or isopropyl, mono-, di-, tri-, tetra-, penta-, hexa-, or hepta-substituted with fluorine. Specific examples are fluoromethyl, trifluoromethyl, 2,2,2-trifluoroethyl, 3-fluoropropyl, 1-methyl-2-fluoroethyl, heptafluoro-n-propyl, and the like.

The term "$C_1$-$C_3$ thioalkyl" means any of methylthio, ethylthio, n-propylthio, and isopropylthio.

The term "$C_1$-$C_3$ hydroxyalkyl" means a $C_1$-$C_3$ alkyl having a hydroxyl group. Examples are hydroxymethyl, 2-hydroxyethyl, 3-hydroxypropyl, and the like.

While all of the compounds of the present invention are useful for treating a variety of disorders which have been linked to decreased neurotransmission of serotonin in mammals (or as intermediates to such compounds), certain of the compounds are preferred. Thus, X preferably is —$CH_2CH_2$—. Also, when $R_4$ is other than hydrogen, $R_1$ preferably is methyl, and when $R_2$ is other than hydrogen, $R_1$ preferably is hydrogen.

When $R_2$ is other than hydrogen, it preferably is alkoxy or halo, and, more preferably, is methoxy or chloro. Most preferably, $R_2$, when not hydrogen, is methoxy. It is also preferred, when $R_2$ is other than hydrogen, that $R_3$ also is other than hydrogen. In particular, when $R_5$ is other than hydrogen, it preferably is halo, and, most preferably, bromo.

When $R_4$ is other than hydrogen, it preferably is halo, and, most preferably, chloro.

The compounds of the present invention possess an asymmetric carbon represented by the carbon atom labeled with an asterisk in the following formula:

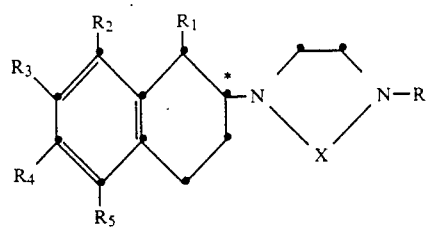

As such, each of the compounds exists as its individual d- and l-stereoisomers as well as the racemic mixture of such isomers. Accordingly, the compounds of the present invention include not only the dl-racemates but also their respective optically active d- and l-isomers.

In addition, when $R_1$ is methyl, a second asymmetric carbon, located at the $R_1$ substituent, is present, giving rise to a further class of stereoisomers.

As mentioned hereinabove, the invention includes pharmaceutically acceptable acid addition salts of the compounds defined by the above formula. Since the compounds of this invention are amines, they are basic in nature and accordingly react with any of a number of inorganic and organic acids to form pharmaceutically acceptable acid addition salts. Since the free amines of the compounds of this invention are typically oils at room temperature, it is preferable to convert the free amines to their corresponding pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, $\beta$-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included as compounds of this invention.

The following compounds further illustrate compounds contemplated within the scope of this invention:
1-Methyl-2'-piperazinyl-8-ethoxy-1,2,3,4-tetrahydronaphthalene;

2-(N-Methylpiperazinyl)-8-ethyl-1,2,3,4-tetrahydronaphthalene;
2-Piperazinyl-8-methylthio-1,2,3,4-tetrahydronaphthalene;
2-Homopiperazinyl-8-ethylthio-1,2,3,4-tetrahydronaphthalene;
1-Methyl-2-piperazinyl-6-ethyl-1,2,3,4-tetrahydronaphthalene;
1-Methyl-2-(N-methylpiperazinyl)-6-ethoxy-1,2,3,4-tetrahydronaphthalene;
1-Methyl-2-homopiperazinyl-6-methylthio-1,2,3,4-tetrahydronaphthalene;
1-Methyl-2-piperazinyl-6-n-propyl-1,2,3,4-tetrahydronaphthalene;
2-Piperazinyl-5-trifluoromethyl-8-iodo-1,2,3,4-tetrahydronaphthalene;
2-N-Methylpiperazinyl)-5-acetyl-8-chloro-1,2,3,4-tetrahydronaphthalene;
2-Homopiperazinyl-5-fluoroacetyl-8-methylthio-1,2,3,4-tetrahydronaphthalene;
2-(N-Methylpiperazinyl)-8-n-propyl-1,2,3,4-tetrahydronaphthalene;
2-Piperazinyl-6-ethylthio-1,2,3,4-tetrahydronaphthalene;
2-(N-Methylpiperazinyl)-6-isopropyl-1,2,3,4-tetrahydronaphthalene; and the like.

The compounds of the present invention may be prepared by procedures well known to those of ordinary skill in the art. The compounds preferably are synthesized by preparation of selected tetralones. The tetralone then is reductively aminated with piperazine, N-methylpiperazine, or the corresponding homopiperazine homologs to produce selected compounds of this invention. Other compounds of this invention are available by modification of the ring substitutents following the reductive amination step.

Schemes for these reactions are as follows:

A. Synthesis of Tetralones

1. 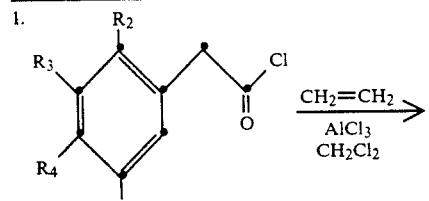

2. 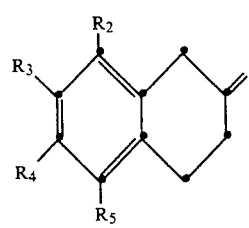

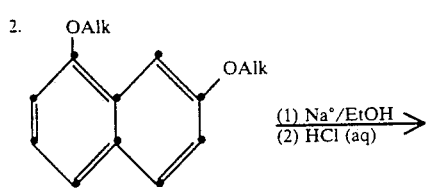

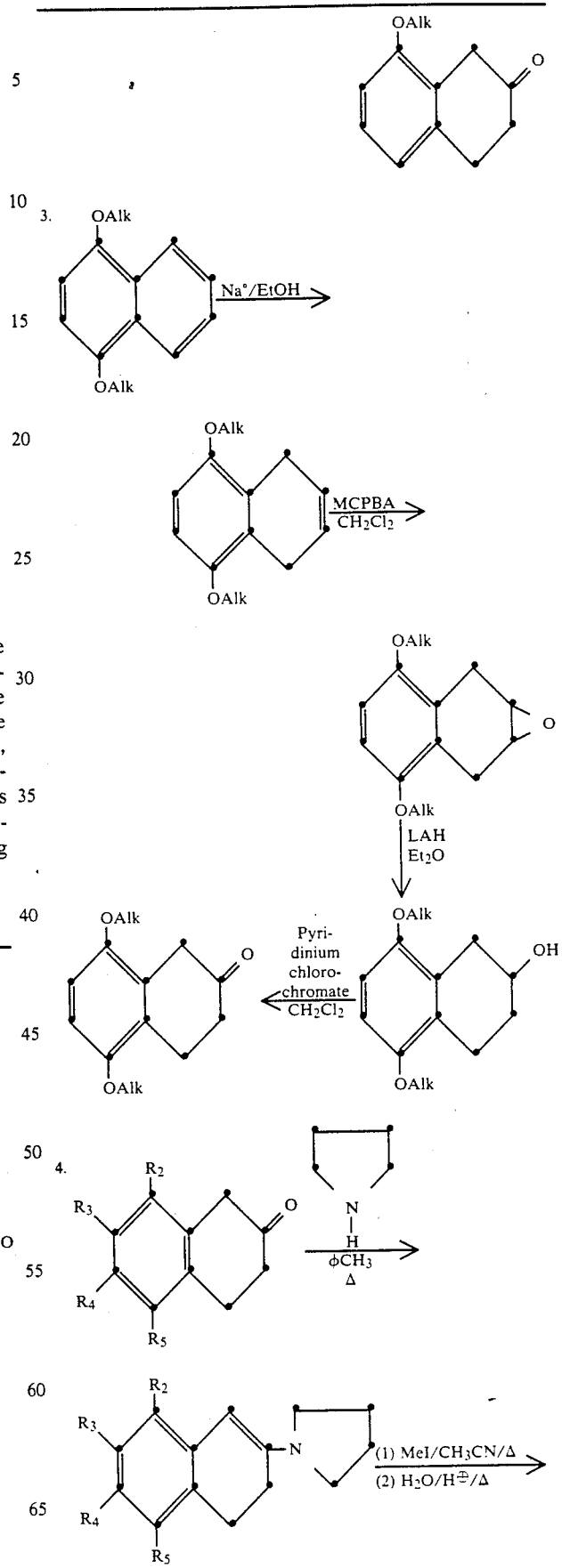

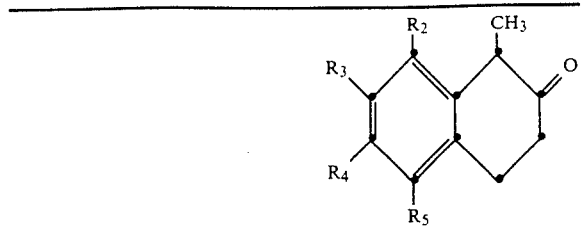

B. Reductive Amination

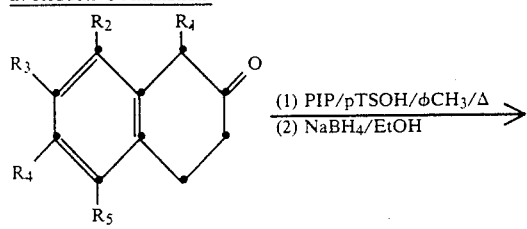

PIP = the unsubstituted or substituted piperazinyl or homopiperazinyl moiety

C. Modification of Aromatic Ring Substituents
1. Bromination

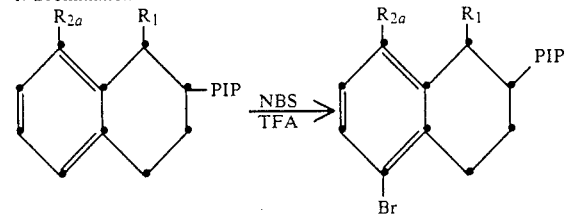

$R_{2a}$ = halo, $C_1$-$C_3$ alkoxy, $C_1$-$C_3$ thioalkyl, $C_1$-$C_3$ alkyl

2. Replacement of Bromo Ring Substituent
a. Via lithiation

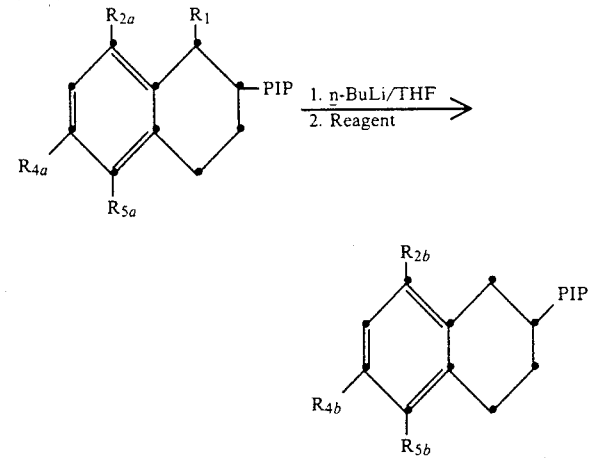

| Bromo | Reagent | Product | Limitations |
|---|---|---|---|
| (1)$R_{2a}$ | (AlkS)$_2$ | $R_{2b}$ = —SAlk | $R_{5a-b}$ = H, alkoxy |
| (2)$R_{4a}$ | (AlkS)$_2$ | $R_{4b}$ = —SAlk | — |
| (3)$R_{5a}$ | | $R_{5b}$ | $R_{2a-b}$ |
| | FOClO$_2$ | F | alkoxy, thioalkyl, alkyl |
| | NCS | Cl | alkoxy, thioalkyl, alkyl |

| | | |
|---|---|---|
| I$_2$ | I | alkoxy, thioalkyl, alkyl |
| C$_1$-C$_3$ acyl-NMe$_2$ | C$_1$-C$_3$ acyl | alkoxy, thioalkyl, alkyl |
| (C$_1$-C$_3$ acyl)$_2$O | C$_1$-C$_3$ acyl | alkoxy, thioalkyl, alkyl |
| (C$_1$-C$_3$ F-subst-acyl)$_2$O | C$_1$-C$_3$ F-subst-acyl | alkoxy, thioalkyl, alkyl |
| TMSNCO | CONH$_2$ | alkoxy, thioalkyl, alkyl |
| CO$_2$ | CO$_2$H | alkoxy, thioalkyl, alkyl | b. 5-Cyano compounds

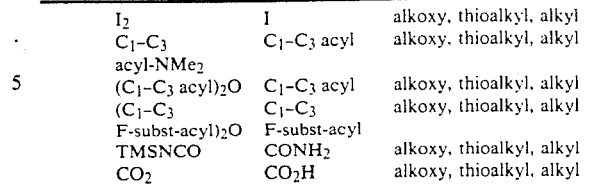

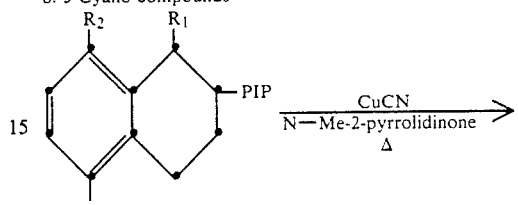

3. Formation of 5-(Fluoro-substituted Alkyl) Compounds

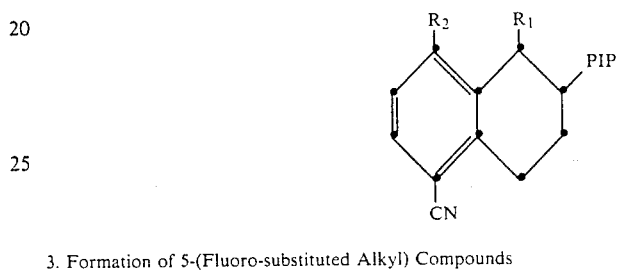

(DAST = Diethylaminosulfur trifluoride)
$R_{2a}$ = halo, alkoxy, thioalkyl, or alkyl.

| $R_{5a}$ | $R_{5b}$ |
|---|---|
| CH$_2$OH | CH$_2$F |
| CHO | CHF$_2$ |
| CO$_2$H | CF$_3$ |

4. Formation of 6- or 8-Hydroxy Compounds

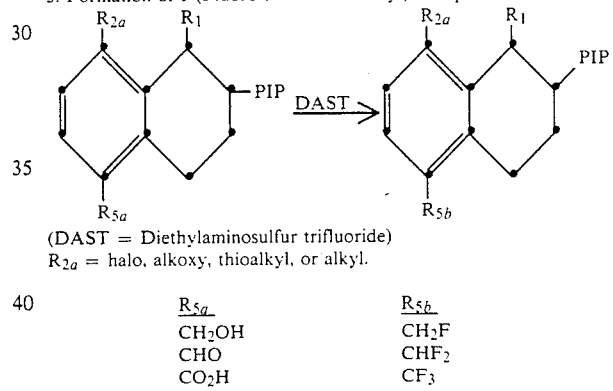

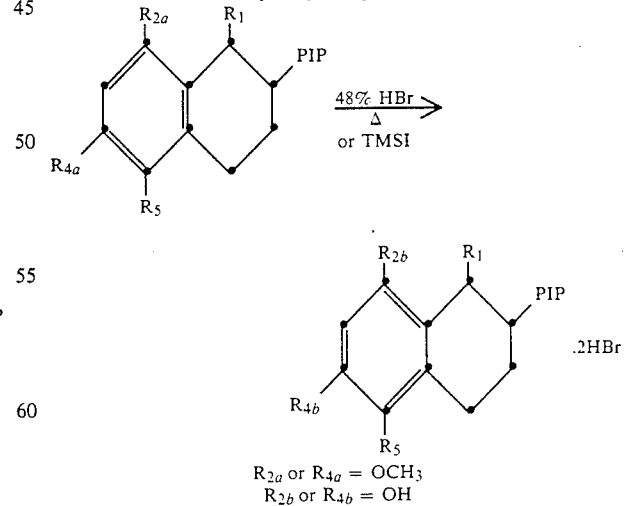

$R_{2a}$ or $R_{4a}$ = OCH$_3$
$R_{2b}$ or $R_{4b}$ = OH

As depicted above, the tetralones represent the intermediate which, when reductively aminated with the piperazine or the homopiperazine compound, result in compounds of this invention or compounds that have the core structure of the compounds of this invention.

The tetralones are available by any of a wide range of recognized methods. For example, they can be produced by a Friedel-Crafts reaction of an appropriately ring-substituted phenylactyl chloride with ethylene in the presence of aluminum chloride.

A 1,7-dialkoxynaphthalene can be reduced with sodium to the corresponding monoalkoxytetralone.

Another method for obtaining a specific tetralone is via the 1,4-dialkoxynaphthalene. The naphthalene is reduced with sodium to the 1,4-dihydronaphthalene, and the latter is oxidized to the corresponding epoxide with m-chloroperbenzoic acid. The epoxide is reduced with lithium aluminum hydride (LAH), and the resulting alcohol is oxidized to the desired product using pyridinium chlorochromate.

When $R_1$ in the compounds of this invention is methyl, the methyl-substituted tetralone can be prepared from the corresponding unsubstituted tetralone. The tetralone first is treated with pyrrolidine to produce the corresponding 1,2-dihydro-3-pyrrolidinylnaphthalene. The latter, upon treatment with methyl iodide and acid hydrolysis, gives the desired 1-methyl-2-tetralone.

The tetralone, once formed, can, by simple reductive amination using unsubstituted or substituted piperazine or homopiperazine (PIP), be converted to a compound of this invention or to one useful as an intermediate to a compound of this invention. The tetralone is first reacted with PIP to form the corresponding enamine after which the enamine is reduced with sodium borohydride to the tetrahydronaphthalene.

Other of the compounds of this invention are available, first by incorporation and then by replacement of a ring substituent on the tetrahydronaphthalene moiety. A compound of this invention having a substituent in the 8-position can be treated with N-bromosuccinimide to produce the corresponding 5-bromo compound.

A tetrahydronaphthalene having a bromo substituent, whether in the 5-, 6-, or 8-position, is useful to produce other compounds of this invention via formation of a lithium intermediate via a lithiation reaction using n-butyllithium. The reactive lithium intermediate can be treated with any of a wide range of electrophilic reagents to produce compounds of this invention. 5 Thus, treatment with a dialkyl disulfide produces an alkylthio substituent, with $FOClO_2$ a fluoro substituent, with N-chlorosuccinimide a chloro substituent, with iodine an iodo substituent, with an N,N-dimethylamide or an acyl anhydride an acyl substituent, with a fluoro-substituted acyl anhydride a fluoro-substituted acyl substituent, with trimethylsilyl isocyanate a carboxamide substituent, and with carbon dioxide a carboxyl substituent.

The 5-bromotetrahydronaphthalene is converted to its corresponding cyano compound by treatment with cuprous cyanide at elevated temperature.

Compounds of this invention in which the 5-substituent is a fluoro-substituted alkyl group are available by treatment of the corresponding alcohol, aldehyde or carboxylic acid with diethylaminosulfur trifluoride (DAST).

Compounds of this invention in which the ring substituent is hydroxy are available from the corresponding alkoxy compound by treatment with 48% hydrobromic acid or trimethylsilyl iodide.

The optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents are d- and l-tartaric acids, d- and l-ditoluyltartaric acids, and the like.

The compounds employed as starting materials in the synthesis of the compounds of this invention are well known and readily synthesized by standard procedures commonly employed by those of ordinary skill in the art.

The pharmaceutically acceptable acid addition salts of the invention are typically formed by reacting a 1,2,3,4-tetrahydronaphthalene of this invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods for their synthesis. The Examples are not intended to be limiting to the scope of the invention in any respect and should not be so construed.

Unless otherwise noted, the NMR data appearing in the following examples refers to the free bases of the subject compounds.

EXAMPLE 1

Preparation of 2-(Methylpiperazinyl)-8-methoxy-1,2,3,4-tetrahydronaphthalene dihydrochloride A. 8-Methoxy-2-tetralone To one liter of acetone were added 50.0 grams (0.31 mol) of 1,7-dihydroxynaphthalene. To the solution then were added 95.0 grams (0.69 mol) of powdered potassium carbonate and 65 ml (0.69 mol) of dimethyl sulfate. The mixture was stirred at reflux under nitrogen for about 18 hours. The mixture then was allowed to cool to room temperature and diluted with 2 liters of water after which it was extracted with methylene chloride. The organic extracts were combined, washed successively with water and saturated aqueous sodium chloride, dried over sodium sulfate, and evaporated in vacuo to give a brown oil.

The oil was distilled in vacuo to obtain 52.51 g (90.1%) of 1,7-dimethoxynaphthalene as a light orange, transparent oil, bp 155–157° C. (4 mm Hg).

NMR (CDCl$_3$): 7.6–6.9(m, 5H), 6.7–6.6(d, J=7.2, 1H), 3.88(s, 3H), 3.84(s, 3H).

The foregoing product (52.5 g; 0.279 mol) was dissolved in 450 ml of ethanol. To the solution then were added 54.4 g (2.37 mol) of sodium at a rate sufficient to maintain a gentle reflux. Nitrogen was passed through the mixture to remove the hydrogen which is being formed. The mixture then was heated at reflux until all of the sodium was consumed after which it was cooled to room temperature, diluted with 300 ml of water followed by 350 ml of concentrated HCl, and then heated on a steam bath for 30 minutes. The mixture was diluted with water until all remaining solid dissolved and then was cooled to room temperature and extracted with ether. The organic extracts were combined, washed with water and then with saturated aqueous sodium chloride, dried over sodium sulfate, and evaporated in vacuo to give a yellow oil. The oil was dissolved in minimal ether and added to about 250 ml of saturated aqueous sodium bisulfite. The two-phase system was stirred vigorously for 18 hours.

The resulting colorless suspension was filtered, and the collected solid was washed with ether and dried in vacuo. The solid then was added to about 300 ml of 50% aqueous potassium carbonate. Ether was added, and the mixture was stirred vigorously until all solid had dissolved. The two-phase mixture then was separated, and the aqueous portion was extracted with ether. The combined ether phases were washed successively with water and saturated aqueous sodium chloride, dried over sodium sulfate, and evaporated in vacuo to give 32.8 g (67%) of the title compound as a colorless, crystalline mass. NMR (CDCl$_3$): 7.2–7.0(t, J=7.2, 1H), 6.8–6.6(t, J=7.2, 2H), 3.76(s, 3H), 3.48(s, 2H), 3.14–2.92(t, J=7.2, 2H), 2.62–2.46(t, J=7.2, 2H).

B.

2-(N-methylpiperazinyl)-8-methoxy-1,2,3,4-tetrahydronaphthalene dihydrochloride

The tetralone (10 g; 56.8 mmol) was dissolved in 200 ml of toluene. To the solution then were added 13.0 ml (0.117 mol) of N-methylpiperazine followed by 25.1 g (0.13 mol) of p-toluenesulfonic acid. The mixture was stirred at reflux with constant removal of water. After 2 hours, the mixture was cooled to room temperature, and the volatiles were removed in vacuo to give 3-(N-methylpiperazinyl)-5-methoxy-1,2-dihydronaphthalene as a reddish-orange sludge.

The sludge was dissolved in 200 ml of ethanol. To the solution were added 30 ml of acetic acid followed by 10 g of sodium borohydride. The mixture was stirred for 2 hours at room temperature after which it was diluted with 200 ml of 10% HCl and then stirred for an additional hour at room temperature. The mixture was diluted with water and extracted with ether. The aqueous layer then was made basic by addition of ammonium hydroxide and extracted with methylene chloride. The methylene chloride extracts were combined, dried over sodium sulfate, and evaporated in vacuo to give a red-brown brown oil. The oil was dissolved in methylene chloride and placed on a flash silica column. The column was eluted with methylene chloride containing 3% MeOH and a trace amount of NH$_4$OH to give a light orange, transparent oil. The oil was triturated with hexane. The resulting mixture was filtered, and the filtrate was evaporated in vacuo to give 7.5 g of a light yellow solid. One gram of the solid was converted to the dihydrochloride salt and crystallized from methanol to provide 1.10 g of the title compound as colorless crystals, m.p. >200° C.

Analysis, calculated for C$_{16}$H$_{24}$N$_2$O.2HCl: Theory: C, 57.66; H, 7.86; N, 8.40. Found: C, 57.46; H, 7.80; N, 8.31.

NMR (CDCl$_3$): 7.12–6.88(t, J=7.2, 1H), 6.76–6.48(m, 2H), 3.76(s, 3H), 3.20–2.36(m, 12H), 2.31(s, 3H), 2.22–1.92 (m, 2H), 1.8–1.2(m, 1H).

MS: 260 (25), 216 (8), 202 (9), 189 (17), 188 (11), 174 (10), 162 (32), 160 (39), 100 (92), 70 (62), 58 (100).

EXAMPLE 2

Preparation of
2-Piperazinyl-8-methoxy-1,2,3,4tetrahydronaphthalene dihydrochloride The tetralone (1.0 g; 5.68 mmol) produced in Example 1 was treated in accordance with the procedure described in Example 1 employing piperazine instead of N-methylpiperazine to produce 0.22 g of a yellow, viscous oil. The oil was treated with gaseous HCl to obtain 0.13 g of the title compound as colorless crystals.

Analysis, calculated for C$_{15}$H$_{22}$N$_2$O.2HCl: Theory: C, 56.43; H, 7.58; N, 8.77. Found: C, 56.22; H, 7.51; N, 8.53.

NMR (CDCl$_3$): 7.22–7.00(t, J=7.2, 1H), 6.84–6.60(m, 2H), 3.91 (s, 3H), 3.28–2.56(m, 12H), 2.45 (s, 1H), 2.36–2.0 (m, 2H), 1.96–1.40 (m, 1H).

MS: 247 (23), 246 (100), 245 (8), 231 (5), 204 (65), 161 (78).

EXAMPLE 3

Preparation of
2-Piperazinyl-8-chloro-1,2,3,4-tetrahydronaphthalene dimaleate

A. 8-Chloro-2-tetralone

A mixture of 30.0 g (0.176 mol) of o-chlorophenylacetic acid and 40 ml of thionyl chloride was stirred for 18 hours. The volatiles then were removed in vacuo to give 32.76 g (99.0%) of o-chlorophenylacetyl chloride as a transparent, pale yellow, mobile liquid.

NMR (CDCl$_3$): 7.5–7.1(m, 4H), 4.2 (s, 2H).

AlCl$_3$ (46.5 g; 0.348 mol) was slurried in 400 ml of methylene chloride. The mixture then was cooled to −78° C., and a solution of 32.76 g (0.174 mol) of the previously produced o-chlorophenylacetyl chloride in 100 ml of methylene chloride was added dropwise over 1 hour. The dry ice/acetone bath then was replaced with an ice water bath. Ethylene was bubbled into the reaction mixture during which time the temperature rose to 15° C. The ethylene addition was discontinued, and the mixture was allowed to stir at about 5° C. for 4 hours. Ice then was added to the mixture to decompose any remaining aluminum complexes. Upon termination of the exotherm, the mixture was diluted with water (500 ml) and stirred vigorously until all of the solid was dissolved. The aqueous and organic phases were separated, and the organic phase was washed 3 times with 400 ml each of 1N HCl and twice with 400 ml each of 10% aqueous sodium bicarbonate. The organic phase then was dried over sodium sulfate and evaporated in vacuo to obtain a pale orange residue. The residue was dissolved in a 1:1 mixture of hexane and ether and applied to a flash silica column which was then eluted with a 1:1 mixture of hexane and ether to give a light yellow residue which was crystallized from a 4:1 mixture of hexane and ether to obtain 10.55 g (33.6%) of the title compound.

NMR (CDCl$_3$): 7.5–7.2(m, 3H), 3.7(s, 2H), 3.3–3.0 (t, J=7, 2H), 2.8–2.4(t, J=7, 2H).

MS: 180 (60), 165 (9), 138 (100), 117 (52), 115 (50), 103 (48), 89 (20), 76 (25), 74 (18), 63 (30), 57 (9), 52 (28), 51 (20), 42 (6), 39 (32).

IR (nujol mull): 2950 cm−, 2927 cm−, 1708 cm−, 1464 cm−, 1450 cm−, 1169 cm−, 1141 cm−

B.

2-Piperazinyl-8-chloro-1,2,3,4-tetrahydronaphthalene dimaleate

The foregoing tetralone (0.5 g; 2.78 mmol) was treated with piperazine and the resulting product reduced with sodium borohydride in accordance with the procedure as described in Example 1. The product was treated with maleic acid to obtain 0.12 g of the title compound, m.p. 180°–181° C.

Analysis. calculated for C-H$_{19}$N$_2$Cl.2C$_4$O$_4$: Theory: C, 54.72; H, 5.64; N, 5.80. Found: C, 54.81; H, 5.67; N, 5.89.

NMR (CDCl$_3$): 7.4–6.8(m, 3H), 3.3–2.6(m, 15H), 2.55 (s, 1H).

MS: 252 (10), 250 (35), 210 (28), 208 (100), 167 (17), 165 (39), 129 (40), 54 (68).

EXAMPLE 4

Preparation of 2-(N-methylpiperazinyl)-8-chloro-1,2,3,4-tetrahydronaphthalene dimaleate Using the method of Example 3, 0.5 g (2.78 mmol) of 8-chloro-2-tetralone was treated with N-methylpiperazine, and the resulting product was reduced with sodium borohydride and the product treated with maleic acid to obtain 0.48 g of the title compound as colorless crystals, m.p. 199°–201° C.

Analysis, calculated for C$_{15}$H$_{21}$N$_2$Cl.2C$_4$H$_4$O$_4$: Theory: C, 55.59; H, 5.88; N, 5.64. Found: C, 55.81; H, 6.02; N, 5.59.

NMR (CDCl$_3$): 7.4–6.8(m, 3H), 3.3–2.4(m, 11H), 2.3 (s, 3H), 2.2–1.0(m, 4H).

MS: 266 (18), 264 (52), 222 (5), 224 (12), 193 (32), 129 (30), 45 (100).

EXAMPLE 5

Preparation of 2-(Homopiperazinyl)-8-chloro-1,2,3,4-tetrahydronaphthalene dimaleate Employing the procedure of Example 3, 2.0 g (11.1 mmol) of 8-chloro-2-tetralone were reacted with 2.2 g (22.2 mmol) of homopiperazine, and the resulting product was reduced with sodium borohydride and the reduced product treated with maleic acid to obtain 0.13 g of the title compound as colorless crystals, m.p. 146°–148° C.

Analysis, calculated for C$_{15}$H$_{21}$N$_2$Cl.2C$_4$H$_4$O$_4$: Theory: C, 55.59; H, 5.88; N, 5.64. Found: C, 55.89; H, 6.02; N, 5.37.

NMR (CDCl$_3$): 7.24–6.80(m, 3H), 3.28–2.48(m, 14H), 2.47(s, 1H), 2.24–1.08(m, 3H).

MS: 266 (17), 265 (12), 264 (49), 224 (5), 222 (20), 20 (15), 210 (18), 209 (21), 208 (55), 207 (48), 206 (16), 196 (19), 194 (22), 165 (48), 129 (24), 98 (42), 2 (75), 54 (100).

EXAMPLE 6

Preparation of 2-(N-methylpiperazinyl)-8-fluoro-1,2,3,4-tetrahydronaphthalene dimaleate

A. 8-Fluoro-2-tetralone o-Fluorophenylacetic acid (35.9 g; 0.233 mmol) was stirred in 40 ml of thionyl chloride for 24 hours at room temperature. Volatile material was removed in vacuo to obtain a yellow, mobile liquid. The liquid was distilled in vacuo to obtain 27.45 g (68.5%) of o-fluorophenylacetyl chloride as a colorless liquid, b.p. 85° C. (4 mm Hg).

NMR (CDCl$_3$): 7.6–6.9(m, 4H), 4.3–4.1(d, J=4, 2H).

Aluminum chloride (42.5 g; 0.32 mol) was stirred in 400 ml of methylene chloride, and the resulting solution was cooled to −78° C. To the solution then was added dropwise a solution of 27.45 q (0.16 mol) of the previously prepared aoyl chloride in 100 ml of methylene chloride over one hour. The dry ice/acetone bath was replaced with an ice water bath, and ethylene was bubbled vigorously into the flask, the temperature rising from −50° to +17° C. Upon completion of the exotherm, the ethylene addition was discontinued, and the reaction mixture was stirred for two hours at about 5° C. and then for two hours at room temperature.

Ice then was cautiously added to the reaction mixture. Upon completion of the resulting exotherm, the reaction mixture was diluted with 500 ml of cold water. The organic and aqueous phases were separated, and the organic phase was washed three times with 100 ml of 1N HCl and twice with 100 ml of saturated aqueous sodium bicarbonate. The organic layer then was dried over sodium sulfate and evaporated in vacuo to obtain a yellow residue. The residue was dissolved in a 1:1 mixture of hexane and ether and placed on a flash silica column. The column was eluted with a 1:1 mixture of hexane and ether to give a yellow viscous residue. The residue was crystallized from a 4:1 mixture of hexane and ether to obtain a total of 5.85 g of the tetralone as a colorless solid.

NMR (CDCl$_3$): 7.4–6.7(m, 3H), 3.6(s, 2H), 3.2–2.9(t, J=6, 2H), 2.7–2.4(t, J=6, 2H).

MS: 164 (100), 149 (23), 140 (8), 138 (31), 136 (17), 135 (57), 134 (12), 133 (40), 123 (31), 122 (100), 120 (41), 115 (24), 109 (26), 107 (18), 101 (22), 96 (34), 89 (7), 83 (16), 75 (17), 63 (22), 57 (21), 51 (17), 39 (18).

IR (KBr pellet): 3436, 3427, 3414, 3401, 1716, 1705, 1495, 1246, 1138, 886 cm$^-$.

B. 2-(N-methylpiperazinyl)-8-fluoro-1,2,3,4-tetrahydronaphthalene dimaleate The foregoing tetralone (1.0 g; 6.1 mmol) was dissolved in 30 ml of toluene. To the solution then were added 1.4 ml (12.2 mmol) of N-methylpiperazine and 2.78 g (14.6 mmol) of p-toluenesulfonic acid. The mixture was heated at reflux for 18 hours with constant water removal after which the mixture was cooled to room temperature. The solvent was removed in vacuo to give 3-(N-methylpiperazinyl)-5-fluoro-1,2-dihydronaphthalene as a reddish orange solid. The dihydronaphthalene was dissolved in 20 ml of ethanol. To the solution were added 1.5 ml of acetic acid followed by a total of about 0.5 g of sodium borohydride added in portions. The resulting mixture was stirred for 2 hours at room temperature after which the mixture was diluted with 10% aqueous HCl and stirred an additional hour at room temperature. The reaction mixture was diluted with water and extracted with ether. The aqueous layer was poured over ice and made basic by addition of ammonium hydroxide. It was then extracted with methylene chloride. The methylene chloride extracts were combined, washed with saturated aqueous sodium chloride, dried over sodium sulfate and evaporated in vacuo to give a brown, viscous oil.

The oil was dissolved in methylene chloride and placed on a flash silica column. The column was eluted with 5% methanol in methylene chloride and a trace of ammonium hydroxide, and the eluate was evaporated in vacuo to give 0.25 g of the free base product as a light yellow, transparent, viscous residue.

The residue was dissolved in methanol, and the solution was heated to boiling. To the solution then were added two equivalents of maleic acid in methanol, and the resulting mixture was heated to boiling. The solution was filtered, and the filtrate was cooled to room temperature with crystal formation. The solution then was cooled to 0° C., and the crystals were filtered and dried in vacuo to give 0.37 g of the title compound as colorless crystals; m.p. 204°–205° C.

Analysis, calculated for $C_{15}H_{21}N_2F \cdot 2C_4H_4O_4$: Theory: C, 57.49; H, 6.08; N, 5.83. Found: C, 57.32; H, 5.97; N, 6.02.

NMR (CDCl$_3$): 7.3–6.8(m, 3H), 3.3–2.4(m, 12H), 2.3(s, 3H), 2.2–1.4(m, 3H).

MS: 249 (17), 248 (100), 247 (13), 204 (27), 190 (14), 189 (11), 179 (21), 177 (68), 176 (22), 150 (51), 148 (58), 100 (76), 70 (83), 58 (93).

Employing the method as described in detail in Examples 3 and 6, the compounds of Examples 7–9 were prepared.

EXAMPLE 7

Preparation of 2-(N-Methylpiperazinyl)-8-methyl-1,2,3,4-tetrahydronaphthalene dihydrochloride.

Analysis, calculated for $C_{16}H_{24}N_2 \cdot 2HCl$: Theory: C, 60.57; H, 8.26; N, 8.83. Found: C, 60.31; H, 8.36; N, 8.62.
NMR (CDCl$_3$): 6.96(s, 3H), 3.12–2.40(m, 12H), 2.36(s, 3H), 2.28–2.0(m, 2H), 2.28(s, 3H), 1.92–1.40(m, 1H).

MS: 245 (15), 244 (81), 243 (8), 201 (10), 200 (20), 185 (19), 183 (10), 174 (17), 173 (51), 172 (23), 145 (63), 143 (63), 129 (58), 100 (88), 70 (62), 58 (100).

EXAMPLE 8

Preparation of 2-(N-Methylpiperazinyl)-5,8-dimethyl-1,2,3,4-tetrahydronaphthalene dimaleate Analysis, calculated for $C_{17}H_{26}N_2 \cdot 2C_4H_4O_4$: Theory: C, 61.21; H, 6.99; N, 5.71. Found: C, 61.06; H, 6.85; N, 5.84.

MS: 260 (18), 258 (94), 243 (6), 214 (13), 200 (12), 187 (28), 186 (13), 144 (15), 143 (31), 100 (62), 72 (60), 58 (100).

EXAMPLE 9

Preparation of 2-(N-Methylpiperazinyl)-8-bromo-1,2,3,4-tetrahydronaphthalene dimaleate Analysis, calculated for $C_{15}H_{21}N_2Br \cdot 2C_4H_4O_4$: Theory: C, 51.03; H, 5.40; N, Found: C, 51.32; H, 5.54; N, 5.42.

NMR (CDCl$_3$): 7.36–7.16(dd, J=3.6, v.2, 1H), 7.0–6.76 (m, 2H), 3.13–2.33(m, 12H), 2.28(s,3H), 2.20–1.86 (m, 2H), 1.76–1.12(m, 1H).

MS: 310 (40), 308 (40), 266 (11), 64 (10) 252 (13), 250 (10), 239 (35), 237 (35), 224 (1'0), 210 (12!), 208 (12), 130 (70), 129 (88), 128 (65), 115 (30), 100 (92), 99 (50), 72 (75), 70 (95), 58 (100) 56 (69), 54 (98).

EXAMPLE 10

Preparation of 2-(N-methylpiperazinyl)-5,8-dimethoxy-1,2,3 dihydrochloride.

A. 5,8-Dimethoxy-2-tetralone

To one liter of acetone were added 50.0 g (0.31 mol) of 1,4-dihydroxynaphthalene. To the resulting solution then were added 95.0 g (0.69 mol) of powdered potassium carbonate and 65 ml (0.69 mol) of dimethyl sulfate. The resulting mixture was stirred at reflux for 18 hours after which it was diluted with two liters of water and then extracted with methylene chloride. The organic extracts were combined, dried over sodium sulfate, and evaporated in vacuo to give a black oil. The oil was distilled in vacuo to give 12.5 g of 1,4-dimethoxynaphthalene as an orange crystalline solid. b.p. 155° C. at 5 mm Hg.

The dimethoxynaphthalene compound (66.5 mmol) was dissolved in 120 ml of ethanol. The resulting mixture was heated to reflux under nitrogen, and 11.7 g (0.51 mol) of sodium were added in portions. Stirring at reflux under nitrogen was continued until all of the solid had dissolved. The mixture then was stirred for 15 minutes at room temperature then cautiously diluted with 50 ml of water. The mixture was evaporated in vacuo to remove ethanol, and the remainder was diluted with water and extracted with ether. The organic extracts were combined, dried over sodium sulfate, and evaporated in vacuo to give 11.1 g of 5,8-dimethoxy-1,4-dihydronaphthalene as a yellow oil.

The dihydronaphthalene (58.4 mmol) was dissolved in 80 ml of methylene chloride. To the solution were added 12.9 g (0.063 mol) of 85% m-chloroperbenzoic acid (MCPBA) in 140 ml of methylene chloride dropwise over 10 minutes. Cooling was required during the addition to maintain the temperature at about 25° C. The mixture then was stirred at room temperature for 45 minutes after which it was washed with saturated aqueous sodium bicarbonate to remove any m-chlorobenzoic acid. The organic phase was washed with water and then with saturated aqueous sodium bicarbonate, dried over sodium sulfate, and evaporated in vacuo to give a brown, viscous tar. The tar was dissolved in ether and placed on a flash silica column. The column was eluted with ether, and Fractions 3–6 were combined and evaporated in vacuo to give a transparent viscous orange oil. The oil was dissolved in a 1:1 mixture of hexane and ether and placed on a flash silica column. The column was eluted with a 2:1 mixture of hexane and ether. Fractions 5–8 were combined and evaporated in vacuo to give 2.35 g of 5,8-dimethoxy-2,3-oxo-1,2,3,4-tetrahydronaphthalene as colorless needles; m.p. 128°–129° C.

The oxo compound (2.35 g; 11.4 mmol) was dissolved in 50 ml of ether, and the solution was added dropwise to a refluxing suspension of 1.53 g of lithium aluminum hydride (LAH) in 100 ml of ether. The resulting mixture was refluxed for five hours and then was cooled to 0° C. To the mixture then were added sequentially and with caution 1.53 ml of water, 1.53 ml of 15% aqueous sodium hydroxide and 4.59 ml of water. The mixture was stirred vigorously for 18 hours at room temperature and then was filtered through a bed of Celite. The bed was washed with ether, and the filtrate was evaporated in vacuo to give 2.1 g (88.6%) of 2-hydroxy-5,8-dimethoxy-1,2,3,4-tetrahydronaphthalene as an off-white solid.

The tetrahydronaphthalene (2.1 g; 10.1 mmol) was dissolved in 20 ml of methylene chloride. The resulting solution was added to a solution of 3.27 g (15.2 mmol) of pyridinium chlorochromate in 60 ml of methylene chloride. The mixture was stirred for seven hours at room temperature and then was filtered through a bed of Celite. The filtrate was evaporated in vacuo to a dark, viscous residue. The residue was dissolved in methylene chloride and placed on a flash silica column. The column was eluted with methylene chloride, and the eluate was evaporated in vacuo to give 0.8 g (38.4%) of 5,8-dimethoxy-2-tetralone as a gold, crystalline solid.

B.
2-(N-Methylpiperazinyl)-5,8-dimethoxy-1,2,3,4-tetrahydronaphthalene dihydrochloride The dimethoxytetralone (0.4 g; 1.94 mmol) was dissolved in 10 ml of toluene. To the solution were added 0.46 ml (4 mmol) of N-methylpiperazine followed by 0.91 g (4.8 mmol) of p-toluenesulfonic acid. The mixture was stirred for 3½ hours at reflux under nitrogen with constant water removal. The mixture then was cooled to room temperature, and the volatile material was removed in vacuo to give 3-(N-methylpiperazinyl)-5,8-dimethoxy-1,2-dihydronaphthalene as an orange-brown residue.

The dihydronaphthalene was dissolved in 10 ml of ethanol. To the resulting solution was added 0.3 g of sodium borohydride in portions. The mixture was stirred for 18 hours at room temperature after which it was diluted with about 15 ml of 10% aqueous HCl. The resulting mixture was stirred for 45 minutes at room temperature and then was diluted with water and extracted with ether. The aqueous layer was made basic with ammonium hydroxide and extracted with methylene chloride. The methylene chloride extracts were combined, dried over sodium sulfate, and evaporated in vacuo to give a dark orange oil.

The oil was dissolved in methylene chloride and placed on a flash silica column. The column was eluted with 3% methanol in methylene chloride and a trace of ammonium hydroxide, and the eluate was evaporated in vacuo to give 0.31 g of the free base of the title compound as a faintly orange glass solid.

The solid was dissolved in ethanol, and the solution was saturated with gaseous HCl. A crystalline solid gradually formed as the solution cooled to give 0.14 g of the dihydrochloride salt of the title compound Analysis, calculated for $C_{17}H_{26}N_2O_2 \cdot 2HCl$: Theory: C, 56.20; H, 7.77; N, 7.71. Found: C, 56.09; H, 7.65; N, 7.78.

NMR (CDCl$_3$): 6.48(s, 2H), 3.69(s, 6H), 3.16–2.32(m, 12H), 2.26(s, 3H), 2.28–1.92(m, 2H), 1.72–1.20(m, 1H).

MS: 291 (11), 290 (50), 289 (8), 275 (8), 246 (10), 232 (10), 231 (13), 219 (16), 218 (12), 191 (53), 190 (100), 164 (36), 99 (48), 43 (88).

EXAMPLE 11

Preparation of
1-Methyl-2-(N-methylpiperazinyl)-8-chloro-1,2,3,4-tetrahydronaphthalene dimaleate

A. 1-Methyl-8-chloro-2-tetralone

To 100 ml of toluene were added 5.0 g (27.8 mmol) of 8-chloro-2-tetralone. To the resulting solution then were added 3.5 g of pyrrolidine, and the mixture was heated to reflux for three hours after which the solvent was removed in vacuo to give 3-pyrrolidino-5-chloro-1,2-dihydronaphthalene as a dark oil (about 6 g).

The dihydronaphthalene was dissolved in 30 ml of p-dioxane. To the solution were added 10 ml of methyl iodide, and the mixture was heated to reflux for 18 hours under nitrogen. To the reaction mixture then were added 25 ml of water and 1 ml of acetic acid, and the heating was continued for four hours. The reaction mixture then was cooled to room temperature, and the solvent was removed in vacuo. The resulting residue was suspended in water, and the aqueous mixture was extracted with ether. The organic extracts were combined, washed with saturated aqueous sodium chloride, dried over sodium sulfate, and evaporated in vacuo to give a dark oil. The oil was dissolved in ether and placed on a flash silica column. The column was eluted with a 1:1 mixture of hexane and ether containing a trace of ammonium hydroxide. The eluate was evaporated in vacuo to give 3.14 g of 1-methyl-8-chloro-2-tetralone as a mobile, orange liquid.

NMR (CDCl$_3$): 7.4–7.0(m, 3H), 4.40–3.70 (q, J=7.2, 1H), 3.32–2.0(m, 4H), 1.52–1.36 (d, J=7.2, 3H).

B.
1-Methyl-2-(N-methylpiperazinyl)-8-chloro-1,2,3,4-tetrahydronaphthalene

The foregoing tetralone (1.0 g; 5.2 mmol) was dissolved in 30 ml of toluene. To the solution were added 1.1 g (10.3 mmol) of N-methylpiperazine and 0.75 ml of methanesulfonic acid, and the mixture was heated to reflux for 18 hours under nitrogen with constant water removal. The reaction mixture was cooled to room temperature, and the solvent was removed in vacuo to give 3-(N-methylpiperazinyl)-4-methyl-5-chloro-1,2-dihydronaphthalene as an orange, viscous residue.

The dihydronaphthalene (about 5.2 mmol) was dissolved in 25 ml of ethanol. To the resulting solution then were added 1.5 ml of acetic acid followed by about 0.5 g of sodium borohydride added in portions. The reaction mixture was stirred for two hours at room temperature after which 30 ml of 10% aqueous HCl were added, and the mixture was stirred for an additional two hours at room temperature. The reaction mixture was diluted with 100 ml of water and extracted once with ether. The aqueous portion was made basic with ammonium hydroxide and extracted with methylene chloride. The methylene chloride extracts were combined, dried over sodium sulfate, and evaporated in vacuo to give a viscous, orange oil.

The oil was dissolved in methylene chloride and placed on a flash silica column. The column was eluted with methylene chloride containing 3% methanol and a trace of ammonium hydroxide, and the eluate was evaporated in vacuo to give 0.41 g of a yellow glass. The glass began to crystallize and the mixture was triturated with hexane. A colorless, crystalline solid was separated by filtration after the mixture was cooled. The colorless solid was found not to be the desired product.

The filtrate then was evaporated in vacuo to give 0.21 g of a pale yellow, transparent glass. The glass was dissolved in methanol and treated with two equivalents of maleic acid in methanol at reflux. The resulting mixture was allowed to cool slowly to room temperature to give 0.30 g of the title compound as a colorless, crystalline solid; m.p. 174–175° C.

Analysis, calculated for $C_{16}H_{23}N_2Cl \cdot 2C_4O_4$: Theory: C, 56.41; H, 6.12; N, 5.48. Found: C, 56.63; H, 6.01; N, 5.49.

NMR (CDCl$_3$): 7.24–6.8(m, 3H), 3.68–3.32 (q, J=7, 1H), 3.0–2.32(m, 10H), 2.30(s, 3H), 2.10–1.20(m, 3H), 1.24–1.08(d, J=7, 3H).

MS: 280 (8), 278 (28), 236 (4), 234 (8), 207 (20), 135 (100), 100 (31), 70 (58), 58 (59), 53 (54), 43 (62).

EXAMPLE 12

Preparation of
1-Methyl-2-piperazinyl-8-chloro-1,2,3,4-tetrahydronaphthalene dihydrochloride Using the method of Example 11, 1.94 g (10 mmol) of 1-methyl-8-chloro-2-tetralone were treated with piperazine followed by reduction with sodium borohydride and treatment with HCl to produce 0.67 g of the title compound as colorless crystals; m.p. >200° C.

Analysis, calculated for $C_{15}H_{21}N_2Cl.2HCl$: Theory: C, 53.35; H, 6.86; N, 8.29. Found: C, 53.13; H, 6.97; N, 8.22.

NMR (CDCl$_3$): 7.28–6.8(m, 3H), 3.72–3.32(m, 1H), 3.16–2.16(m, IOH), 2.24(s, 1H), 2.15–1.44(m, 3H), 1.18–1.04(d, J=7, 3H).

MS: 266 (6), 264 (18), 224 (19), 223 (10), 222 (59), 208 (14), 179 (31).

EXAMPLE 13

Preparation of 1-Methyl-2-piperazinyl-8-methoxy-1,2,3,4-tetrahydronaphthalene tosylate

A. 1-Methyl-8-methoxy-2-tetralone

To 75 ml of toluene were added 3.52 g (20 mmol) of 8-methoxy-2-tetralone followed by 2.5 g of pyrrolidine. The mixture was heated to reflux for three hours after which the solvent was evaporated in vacuo to give 3-pyrrolidino-5-methoxy-1,2-dihydronaphthalene as a dark oil.

The oil was dissolved in 25 ml of p-dioxane. To the solution then were added 7.5 ml of methyl iodide, and the mixture was stirred for 18 hours at reflux under nitrogen. The mixture then was diluted with 25 ml of water and 1 ml of glacial acetic acid, after which it was stirred for 3 hours at reflux. The mixture then was cooled to room temperature, and the volatile materials were removed in vacuo. The resulting residue was suspended in water, and the aqueous mixture was extracted with ether. The organic extracts were combined, washed with saturated aqueous sodium chloride, dried over sodium sulfate, and evaporated in vacuo to give 3.5 g of a brown oil. The oil was dissolved in a 1:1 mixture of hexane and ether and placed on a flash silica column. The column was eluted with a 1:1 mixture of hexane and ether, and the eluate was evaporated in vacuo to give 3.27 g (86.5%) of the title tetralone as a light brown transparent oil.

B. 1-Methyl-2-piperazinyl-8-methoxy-1,2,3,4-tetrahydronaphthalene

The foregoing tetralone (3.27 g; 17.3 mmol) was dissolved in 150 ml of toluene. To the solution then were added 3.04 g (34.6 mmol) of piperazine followed by 7.2 g (38.2 mmol) of p-toluenesulfonic acid. The mixture was stirred at reflux under nitrogen with constant water removal. After 2 hours, the reaction mixture was cooled to room temperature, and the volatiles were removed in vacuo to obtain 3-piperazinyl-4-methyl-5-methoxy-1,2-dihydronaphthalene tosylate as a light yellow solid.

The solid was suspended in about 250 ml of ethanol. To the mixture were added in portions 2.4 g of sodium borohydride. The mixture was stirred for 18 hours at room temperature. The reaction mixture then was diluted with 10% aqueous HCl, after which it was further diluted with water and then extracted with ether. The aqueous layer was made basic with ammonium hydroxide and extracted with a 3:1 mixture of chloroform and isopropyl alcohol. The organic layers were combined, dried over sodium sulfate, and evaporated in vacuo to give a yellow oil. The oil was dissolved in methylene chloride and placed on a flash silica column. The column was eluted with methylene chloride containing 5% methanol and a trace of ammonium hydroxide. The eluate was evaporated in vacuo to give 0.35 g of the title compound as a yellow glass.

NMR (CDCl$_3$): 7.2–6.42(m, 3H), 3.76(s, 3H), 3.6–3.2 (m, 1H), 3.04–2.40(m, 13H), 2.0–1.40(m, 1H), 1.28–1.16 (d, J=7), 1.13–1.00(d, J=7).

EXAMPLE 14

Preparation of 2-(N-Methylpiperazinyl)-8-hydroxy-1,2,3,4-tetrahydronaphthalene dihydrobromide The free base of the product from Example 1 (3.0 g; 11.5 mmol) was dissolved in 25 ml of 48% aqueous HBr, and the mixture was stirred at reflux for three hours. The resulting suspension was cooled to room temperature, and the solvent was removed in vacuo to give a pink solid residue. The residue was triturated with ethanol, and the solid was filtered in vacuo, washed with ethanol and then with ether. The resulting solid was dried in vacuo to give 4.35 g (89.6%) of the title compound as a beige solid.

Analysis, calculated for $C_{15}H_{22}N_2O$ .2HBr: Theory: C, 44.14; H, 5.93; N, 6.86. Found: C, 44.15; H, 5.66; N, 6.73.

NMR (D$_2$O) (as dihydrobromide salt): 7.16–6.92(t, J=7, 1H), 6.80–6.56(d, J=7, 2H), 3.40–2.64(m, 12H), 3.06(s, 3H), 2.60–2.20(m, 2H), 2.08–1.48(m, 1H).

EXAMPLE 15

Preparation of 2-(N-Methylpiperazinyl)-5-bromo-8-methoxy-1,2,3,4-tetrahydronaphthalene dihydrochloride The free base of the product from Example 1 (0.23 g; 0.88 mmol) was dissolved in 10 ml of trifluoroacetic acid (TFA). N-bromosuccinimide (0.16 g; 0.88 mmol) (NBS) was added, and the mixture was stirred for 18 hours at room temperature. The reaction mixture then was poured over ice, made basic with ammonium hydroxide, and extracted with methylene chloride. The methylene chloride extracts were combined, dried over sodium sulfate, and evaporated in vacuo to give 0.27 g of a colorless glass. The free base colorless glass was converted to the dihydrochloride salt which was crystallized from ethanol to obtain 0.12 g of colorless crystals; m.p. >225° C.

Analysis, calculated for $C_{16}H_{23}N_2OBr.2HCl$: Theory: C, 46.62; H, 6.11; N, 6.80. Found: C, 46.49: H, 6.25; N, 6.86.

NMR (CDCl$_3$): 7.32–7.08(d, J=9, 1H), 6.56–6.36(d, J=9, 1H), 3.76(s, 3H), 3.20–2.32(m, 12H), 2.32–1.92(m, 2H), 2.28(s, 3H), 1.80–1.20(m, 1H).

MS: 340 (25), 338 (27), 269 (10), 267 (10), 238 (18), 188 (11), 160 (30), 100 (100), 58 (96).

EXAMPLE 16

Preparation of 2-Piperazinyl-5-bromo-8-methoxy-1,2,3,4-tetrahydronaphthalene dihydrochloride Employing the method described in Example 15, the free base of the product from Example 2 (0.50 g; 2.03 mmol) was converted to the title compound using NBS, TFA, and HCl. The product (0.34 g) was recovered as a colorless solid.

Analysis, calculated for $C_{15}H_2N_2OBr.2HCl$: Theory: C, 45.25; H, 5.82; N, 7.04. Found: C, 4S.37; H, 5.72; N, 7.11.

NMR (CDCl$_3$): 7.32–7.08(d, J=9, 1H), 6.56–6.36(d, J=9, 1H), 3.72(s, 3H), 3.20–2.30(m, 12H), 2.30–1.92(m, 2H), 1.80(s, 1H), 1.76–1.16(m, 1H).

MS: 327 (38), 326 (68), 325 (47), 324 (62), 284 (99), 282 (100), 241 (48), 239 (50), 160 (63).

EXAMPLE 17

Preparation of 2-(N-methylpiperazinyl)-5-bromo-8-methyl-1,2,3,4-tetrahydronaphthalene dihydrochloride Employing the method of Example 15, 0.41 g (1.68 mmol) of the free base of the product from Example 7 was treated with NBS, TFA, and HCl to produce 0.25 g of the title compound as colorless crystals, m.p. >225° C.

Analysis, calculated for $C_{16}H_{23}N_2Br·2HCl$: Theory: C, 48.50; H, 6.36; N, 7.07. Found: C, 48.41; H, 6.15; N, 6.97.

NMR (CDCl$_3$): 7.28–7.12(d, J=7, 1H), 6.84–6.66(d, J=7, 1H), 3.28–2.32(m, 12H), 2.32–1.88(m, 2H), 2.28(s, 3H), 2.12(s, 3H), 1.80–1.20(m, 1H).

MS: 324 (12), 322 (14), 253 (18), 251 (18), 224 (8), 222 (10), 143 (53), 100 (80), 58 (100).

EXAMPLE 18

Preparation of 2-(N-methylpiperazinyl)-8-methylthio-1,2,3,4-tetrahydronaphthalene dimaleate.

The free base of the product from Example 9 (0.66 g; 2.13 mmol) was dissolved in 15 ml of ether, and the solution was cooled to -90° C. Tetrahydrofuran (2 ml) was added to maintain homogeneity. To the mixture then were added 1.4 ml (2.35 mmol) of n-butyllithium (1.6M in hexane), and the mixture was stirred for 30 minutes. To the mixture then was added 0.8 ml (8.52 mmol) of dimethyl disulfide, and the mixture was allowed to warm gradually to room temperature. The reaction mixture then was poured into water, and the aqueous layer was extracted with ether. The organic materials were combined, dried over sodium sulfate, and evaporated in vacuo to give 0.60 g of a yellow oil. The oil (0.10 g) was converted to the dihydrochloride salt in ethanol. The resulting colorless solid was recrystallized from a mixture of ethanol and ether. The resulting salt is crystalline but extremely hygroscopic. The material therefore was converted to the free base and then to the title compound which was crystallized from ethanol to obtain 0.09 g of colorless crystals, m.p. 189.5–190° C.

Analysis, calculated for $C_{16}H_{24}N_2S·2C_4H_4O_4$: Theory: C, 56.68; H, 6.37; N, 5.51. Found: C, 56.96; H, 6.37; N, 5.42.

NMR (CDCl$_3$): 7.36–6.70(m, 3H), 3.20–2.24(m, 12H), 2.44(s, 3H), 2.30(s, 3H), 2.24–1.92(m, 2H), 1.86–1.08 (m, 1H).

MS: 277 (9), 276 (42), 275 (6), 261 (7), 232 (8), 218 (10), 205 (28), 176 (39), 129 (60), 100 (98), 59 (100).

EXAMPLE 19

Preparation of 1-Methyl-2-piperazinyl-5-bromo-8-methoxy-1,2,3,4-tetrahydronaphthalene dihydrochloride To 15 ml of trifluoroacetic acid was added 0.35 g (1.35 mmol) of the product from Example 13. The resulting solution was cooled to 0° C., and 0.240 g (1.35 mmol) of N-bromosuccinimide (NBS) was added. The mixture was stirred at room temperature for 2 hours after which it was poured over ice and made basic with ammonium hydroxide. The resulting mixture was extracted with a 3:1 mixture of chloroform and isopropyl alcohol. The organic extracts were combined, washed with saturated aqueous sodium chloride, dried over sodium sulfate, and evaporated in vacuo to give 0.44 g of a yellow, viscous residue. The residue was dissolved in methylene chloride and placed on a flash silica column. The column was eluted with methylene chloride containing 5% methanol and a trace of ammonium hydroxide. Fraction 7 was concentrated in vacuo to give 0.28 g of a light yellow glass which was a mixture of cis and trans-isomers of the title compound free base. Fractions 8–9 were combined and concentrated in vacuo to give 0.07 g of the free base of the title compound as a light yellow glass.

Fraction 7 was rechromatographed under identical conditions. Fractions 13–14 were concentrated in vacuo to give 0.12 g of a colorless glass which was shown by NMR to be identical to fractions 8–9 of the previous column. These two lots were combined to give 0.19 g of the title compound free base which was converted to the dihydrochloride salt. Recrystallization from ethanol/acetone gave 0.08 g of the title compound as a colorless, crystalline solid (m.p. >225° C.).

Analysis, calculated for $C_{16}H_{23}N_2OBr·2HCl$: Theory: C, 46.62; H, 6.11; N, 6.80. Found: C, 46.35; H, 6.35; N, 6.82.

NMR (CDCl$_3$): 7.32–7.08(d, J=9, 1H), 6.56–6.36(d, J=9, 1H), 3.76(s, 3H), 3.6–3.2(m, 1H), 3.16–2.32(m, 10H), 2.32–1.90(m, 2H), 2.16(s, 1H), 1.90–1.30(m, 1H), 1.16–0.96(d, J=7, 3H)

MS: 341 (19), 339 (20), 299 (52), 296 (60), 284 (10), 282 (12), 174 (33), 111 (48), 56 (71).

EXAMPLE 20

Preparation of 2-(N-Methylpiperazinyl)-5-fluoro-8-methoxy-1,2,3,4-tetrahydronaphthalene dimaleate The free base of the product from Example 15 (0.25 g; 0.737 mmol) was dissolved in 10 ml of THF. The solution was cooled to -78° C., and 0.52 ml of n-butyllithium (1.6M in hexane) was added. The mixture was stirred for 30 minutes at -78° C.

Perchloryl fluoride was bubbled into the reaction mixture, and the color changed immediately to an emerald green. The mixture was allowed to warm gradually to room temperature during which the color changed to a reddish brown with the presence of a suspended solid. About 3 ml of 10% potassium hydroxide in methanol were added, and the mixture changed to a yellow-brown suspension. The mixture was stirred for one hour at room temperature.

The reaction mixture then was poured into water and extracted with ether. The organic phases were combined, dried over sodium sulfate, and evaporated in vacuo to give 0.16 g of an orange, viscous residue. The residue was dissolved in a 1:1 mixture of THF and hexane and placed on a flash silica column. The column was eluted with a 1:1 mixture of THF and hexane containing a trace amount of ammonium hydroxide to give 0.079 g of a yellow glass.

The glass was dissolved in ethanol, and two equivalents of maleic acid in hot ethanol were added. The mixture was cooled to room temperature to obtain 0.053 g of the title compound as colorless crystals, m.p. 198°–199° C.

Analysis, calculated for $C_{16}H_{23}N_2OF \cdot 2C_4H_4O_4$: Theory: C, 56.47; H, 6.12; N, 5.48. Found: C, 56.75; H, 6.25; N, 5.45.

NMR (CDCl$_3$): 6.84–6.36(m, 2H), 3.73(s, 3H), 3.2–2.16 (m, 12H), 2.28(s, 3H), 2.16–1.72(m, 2H), 1.72–1.20(m, 1H).

MS: 278 (30), 260 (9), 234 (8), 230 (10), 207 (19), 180 (22), 178 (34), 100 (97), 58 (100).

EXAMPLE 21

Preparation of 2-(N-methylpiperazinyl)-5-chloro-8-methoxy-1,2,3,4-tetrahydronaphthalene dihydrochloride The free base of the product from Example 15 (0.24 g; 0.71 mmol) was dissolved in 5 ml of ether. The solution was cooled to −90° C., and about 7 ml of THF were added to make the mixture homogeneous. To the mixture then was added 0.46 ml of n-butyllithium (1.6M in hexane), and the mixture was stirred for 20 minutes at −90° C. To the mixture then was added 0.095 g (0.71 mmol) of N-chlorosuccinimide in 2 ml of THF. The mixture then was allowed to warm gradually to room temperature.

The reaction mixture was diluted with water and extracted with ether. The ether phases were combined, dried over sodium sulfate, and evaporated in vacuo to give 0.21 g of a yellow glass. The glass was dissolved in methylene chloride and placed on a flash silica column. The column was eluted with methylene chloride containing 3% methanol and a trace of ammonium hydroxide to give 0.14 g of a colorless glass.

The mixture then was treated with HCl in ethanol, and the product was fractionally crystallized from ethanol to obtain the title compound.

Analysis, calculated for $C_{16}H_{23}N_2OCl \cdot 2HCl$: Theory: C, 52.26; H, 6.85; N, 7.62. Found: C, 52.30; H, 6.83; N, 7.55.

NMR (CDCl$_3$): 7.10–6.92(d, J=9, 1H), 6.57–6.40(d, J=9, 1H), 3.72(s, 3H), 3.20–2.32(m, 12H), 2.26(s, 3H), 2.32–1.90(m, 2H), 1.76–1.20(m, 1H).

MS: 296 (10), 294 (28), 252 (3), 250 (7), 223 (14), 194 (18), 159 (19), 100 (75), 58 (100).

EXAMPLE 22

Preparation of 2-(N-methylpiperazinyl)-5-iodo-8-methoxy-1,2,3,4-tetrahydronaphthalene dihydrochloride The free base of the product from Example 15 (0.24 g; 0.71 mmol) was dissolved in 5 ml of ether. The resulting solution was cooled to −78° C., and 5 ml of THF were added to maintain homogeneity. To the mixture then was added 0.46 ml of n-butyllithium (1.6M in hexane). The mixture was stirred for 30 minutes at −78° C., and 0.18 g (0.71 mmol) of iodine in 2 ml of THF was added. The mixture then was allowed to warm to room temperature and was diluted with water and extracted with ether. The organic phases were combined, washed with saturated aqueous sodium chloride, dried over sodium sulfate, and evaporated in vacuo to give a yellow oil. The oil was dissolved in methylene chloride and placed on a flash silica column. The column was eluted with methylene chloride containing 3% methanol and a trace amount of ammonium hydroxide to give 0.13 g of a colorless glass. The glass crystallized upon standing and was dissolved in ethanol and the solution saturated with gaseous HCl to obtain 0.06 g of the title compound as a crystalline solid, m.p. >210 C.

Analysis, calculated for $C_{16}H_{23}N_2OI \cdot 2HCl$: Theory: C, 41.85; H, 5.49; N, 6.10. Found: C, 42.12; H, 5.63; N, 6.19.

NMR (CDCl$_3$): 7.56–7.36(d, J=7, 1H), 6.4–6.2(d, J=7, 1H), 3.72(s, 3H), 3.16–2.32(m, 12H), 2.28(s, 3H), 2.32–1.90(m, 2H), 1.84–1.20(m, 1H)

MS: 386 (19), 315 (15), 286 (20), 259 (7), 231 (8), 160 (29), 100 (100), 58 (77).

EXAMPLE 23

Preparation of 2-(N-methylpiperazinyl)−5-formyl-8-methoxy-1,2,3,4-tetrahydronaphthalene dihydrochloride hydrate The free base of the product from Example 15 (0.24 g; 0.71 mmol) was dissolved in 5 ml of ether. The solution was cooled to −90° C., and 0.46 ml (0.74 mmol) of n-butyllithium (1.6M in hexane) was added along with 5 ml of THF to assist in dissolution of the starting material. The solution became orange but remained transparent. The mixture was stirred for 20 minutes at −90° C., after which 60 %1 (0.78 mmol) of N,N-dimethylformamide (DMF) was added. The mixture was allowed to warm gradually to room temperature. The mixture was then poured into water and extracted with ether. The ether phases were combined, washed with saturated aqueous sodium chloride, dried over sodium sulfate, and evaporated in vacuo to give 0.15 g (83.3%) of a pale yellow glass.

The glass was dissolved in ethanol, and the solution was saturated with gaseous HCl. The mixture was cooled to room temperature and a small amount of ether was added to provide a cloudy solution. The resulting solid was recovered and recrystallized from a mixture of methanol and ether to obtain 90 mg of the title compound as colorless crystals, m.p. >200° C.

Analysis, calculated for $C_{17}H_{24}H_2O_2 \cdot 2HCl \cdot H_2O$ Theory: C, 53.83; H, 7.44; N, 7.39. Found: C, 53.62; H, 7.36; N, 7.09.

NMR (CDCl$_3$): 10.0(s, 1H), 7.64–7.42(d, J=7.5, 1H), 6.8–6.6(d, J=7.5, 1H), 3.86(s, 3H), 3.76–3.32(m, 2H), 3.20–2.32(m, 10H), 2.28(s, 3H), 2.28–1.88(m, 2H), 1.80–1.20(m, 1H).

MS: 288 (75), 244 (9), 218 (18), 217 (22), 190 (67), 99 (100), 58 (85).

EXAMPLE 24

Preparation o 2-(N-methylpiperazinyl)-5-cyano-8-methoxy-1,2,3,4-tetrahydronaphthalene dihydrochloride The free base of the product from Example 15 (0.34 g; 1 mmol) was dissolved in 3 ml of N-methyl-2-pyrrolidinone. To the resulting solution was added 0.11 g (1.25 mmol) of cuprous cyanide and the mixture was stirred for 45 minutes at 100° C. under nitrogen. During the course of the reaction, a colorless solid began to form, and the mixture was diluted with 3 ml of N-methyl-2-pyrrolidinone, and the resulting colorless suspension was stirred vigorously. There was no apparent reaction after the 45 minutes at 100° C. The temperature therefore was increased to 130° C., and the solid dissolved with formation of a transparent, yellow-brown solution. The mixture was stirred for one hour at 130° C., still with no evidence of reaction. The reaction mixture then was heated to 150° C., and one equivalent of cuprous iodide was added (0.19 g). The mixture was stirred for 18 hours at 150° C. under nitrogen.

The reaction mixture then was poured over ice and diluted with methylene chloride. The mixture then was filtered through a bed of Celite, and the filter pad was washed with methylene chloride. The organic and aqueous phases of the filtrate then were separated. The organic phase was washed with water, then with saturated aqueous sodium chloride, dried over sodium sulfate, and evaporated in vacuo to give a dark residue. The residue was dissolved in methylene chloride and placed on a flash silica column. The column was eluted with methylene chloride containing 3% methanol and a trace of ammonium hydroxide to give 0.14 g of a brown glass. The glass was treated with gaseous hydrogen chloride, and 0.05 g of the title compound was crystallized from ethanol as colorless crystals, m.p. >200° C.

Analysis, calculated for $C_{17}H_{23}N_3O \cdot 2HCl$: Theory: C, 56.99; H, 7.03; N, 11.73. Found: C, 56.77; H, 6.79; N, 11.52.

NMR (CDCl$_3$): 7.48–7.28(d, J=7.5, 1H), 6.72–6.52 (d, J=7.5, 1H), 3.82(s, 3H), 3.16–2.32(m, 12H), 2.28(s, 3H), 2.32–1.88(m, 2H), 1.84–1.32(m, 1H).

MS: 286 (15) 285 (70), 284 (7), 257 (6), 255 (5), 241 (12), 227 (12), 214 (28), 185 (25), 125 (30), 100 (42), 70 (100), 58 (87).

EXAMPLE 25

Preparation of 2-Piperazinyl-6-chloro-1,2,3,4-tetrahydronaphthalene dihydrochloride.

A mixture consisting of 6-chloro-2-tetralone (5.41 g), piperazine (5.16 g), and 4A molecular sieves (8 g) in 100 ml of dry toluene was heated at reflux with stirring for a short period of time under nitrogen. The toluene was evaporated, and 100 ml of THF and 10 ml of methanol were added to the residue. Sodium cyanoborohydride (1.86 g) was added, the solution was stirred in the cold under nitrogen, and gaseous HCl was added portionwise periodically above the surface until the reaction solution remained acidic. After stirring at room temperature overnight, the sieves were filtered off, and the filtrate was evaporated to dryness. The residue was partitioned between 1N HCl and ether; the aqueous phase was separated and extracted twice with ether. The solution was made basic with sodium hydroxide. The oil which formed was extracted into ether, and the ether solution was dried over Na$_2$SO$_4$. Evaporation of the ether left of a solid (5.1 g). A solution of the solid in ethanol was treated with excess gaseous HCl. After chilling for a period of time, the crystals which had separated were filtered and washed with ethanol. After recrystallization from methanol there was obtained 2.64 g of the title compound. m.p. 264–265° C.

Analysis, calculated for $C_{14}H_{21}Cl_3N_2$: Theory: C, 51.95; H, 6.54; N, 8.65. Found: C, 52.17; H, 6.60; N, 8.71.

EXAMPLE 26

Preparation of 2-Piperazinyl-6-bromo-1,2,3,4-tetrahydronaphthalene dihydrochloride By the method described in Example 25, the title compound was prepared from 6-bromo-2-tetralone. m.p. 258–260° C. (ethanol).

Analysis calculated for $C_{14}H_{21}BrCl_2N_2$: Theory: C, 45.68; H, 5.75; N, 7.61. Found: C, 45.65; H, 6.01; N, 7.85.

EXAMPLE 27

Preparation of 2-Piperazinyl-6-fluoro-1,2,3,4-tetrahydronaphthalene dihydrochloride By the method described in Example 25 using 3A instead of 4A molecular sieves, the title compound was prepared from 6-fluoro-2-tetralone. m.p. 243–245° C (ethanol).

Analysis, calculated for $C_{14}H_{21}Cl_2FN_2$: Theory: C, 54.73; H, 6.89; N, 9.12. Found: C, 54.48; H, 6.62; N, 9.22.

EXAMPLE 28

Preparation of 2-Piperazinyl-6-methyl-1,2,3,4-tetrahydronaphthalene dihydrochloride In general, by the method described in Example 25, the title compound was prepared from 6-methyl-2-tetralone. m.p. 266–268° C. (methanol).

Analysis, calculated for $C_{15}H_{24}N_2$: Theory: C, 59.41; H, 7.98; N, 9.24. Found: C, 59.61; H, 7.87; N, 8.99.

EXAMPLE 29

Preparation of 2-Piperazinyl-6-methoxy-1,2,3,4-tetrahydronaphthalene dihydrochloride In general, by the method described in Example 25, the title compound was prepared from 6-methoxy-2-tetralone m.p. 264–266° C. (methanol).

Analysis, calculated for $C_{15}H_{24}Cl_2N_2O$:

Theory: C, 56.43; H, 7.58; N, 8.77. Found: C, 56.26; H, 7.42; N, 8.50.

EXAMPLE 30

Preparation of 2-Piperazinyl-6,7-dichloro-1,2,3,4-tetrahydronaphthalene dihydrochloride A mixture consisting of 6,7-dichloro-2-tetralone (4.30 g), piperazine (3.44 g), and 4A molecular sieves (4 g) 100 ml of toluene was stirred overnight under nitrogen and warmed briefly. The sieves were filtered off, and the filtrate was freed of solvent on an evaporator. Seventy-five ml of THF and 6 ml of methanol were added to the residue. The solution was cooled in an ice bath under nitrogen, and 1.24 g of sodium cyanoborohydride was added. Small amounts of gaseous HCl were added periodically until the solution remained acidic. The solution was stirred overnight at ambient temperature, the solvents were evaporated, and the residue was dissolved in dilute HCl. The acidic solution was extracted with three portions of ether and then made basic with sodium hydroxide. The oil which separated was extracted with ether, and the ether solution was dried (Na$_2$SO$_4$). The after evaporation of the ether was dissolved in ethanol, and excess anhydrous HCl was added. The crystalline solid isolated from the ethanol melted at about 272°–275° C. After recrystallization from ethanol there was obtained 1.1 g of the title compound. m.p. 278°–282° C.

Analysis, calculated for $C_{14}H_{20}Cl_4N_2$: Theory: C, 46.95; H, 5.63; N, 7.84. Found: C, 47.22; H, 5.54; N, 7.74.

EXAMPLE 31

Preparation of
2-(N-Methylpiperazinyl)-6-bromo-1,2,3,4-tetrahydronaphthalene dihydrochloride A mixture of 6-bromo-2-tetralone (4.50 g), N-methylpiperazine (4.0 g), and potassium carbonate (5.52 g), in 75 ml of THF was stirred for about one hour. The solids were filtered and sodium cyanoborohydride (1.24 g), was added to the filtrate. To the stirred solution at room temperature was added portionwise sufficient ethereal HCl to make the solution acidic. When NMR analysis of a sample of the reaction solution showed the absence of the vinyl proton of the intermediate enamine, the solvents were evaporated. The residue was partitioned between ether and 1N HCl, and the ether phase was discarded. The aqueous phase was made basic, and the organic material which separated was extracted into ether and ethyl acetate. The extracts were dried ($Na_2SO_4$). The solvents were evaporated, and the residual basic material in ethanol was treated with excess hydrochloric acid. There was obtained 4.41 g of the title compound. m.p. 270°–272° C. (dec).

Analysis, calculated for $C_{15}H_{23}N_2BrCl_2$: Theory: C, 47.14; H, 6.07; N, 7.33. Found: C, 46.99; H, 5.95; N, 7.54.

EXAMPLE 32

Preparation of
2-(N-Methylpiperazinyl)-6-chloro-1,2,3,4-tetrahydronaphthalene dihydrochloride In general, using 6-chloro-2-tetralone in place of 6-bromo-2-tetralone in the method described by Example 31, the title compound was obtained m.p. 269°–271° C. (ethanol).

Analysis, calculated for $C_{15}H_{23}N_2Cl_3$: Theory: C, 53.35; H, 6.86; N, 8.29. Found: C, 53.11; H, 6.68; N, 8.23.

EXAMPLE 33

Preparation of
cis-1-Methyl-2-piperazinyl-6-chloro-1,2,3,4-tetrahydronaphthalene dihydrochloride A solution of 13.7 g of 6-chloro-2-tetralone and 12.7 ml of pyrrolidine in 250 ml of dry benzene was refluxed under a Dean-Stark water trap for 17 hours. The benzene and excess pyrrolidine were removed on a rotary evaporator. Dry toluene was added to the residue and then evaporated, leaving a crystalline residue.

NMR ($CDCl_3$): 1.9(m, 4H), 2.17–2.54(m, 2H), 2.54–2.93(m, 2H), 3.25(m, 4H), 5.07(s, 1H), 6.62–7.42(m, 3H).

The solid was dissolved in 100 ml of dry dioxane, 24 ml of methyl iodide was added, and the solution was refluxed for about three and one-half hours. Crystalline solid started to separate after about one-half hour. A solution containing one ml of acetic acid in 50 ml of water was added to the reaction mixture, and the whole was refluxed for about three and one-half hours. Solvents were evaporated, and the residue was partitioned between water and ether. The ether phase was separated, extracted with a small amount of dilute hydrochloric acid, and dried. Removal of the solvent left about 12 g of an oil. Preparative HPLC gave 9.3 g of 6-chloro-1-methyl-2-tetralone.

NMR ($CDCl_3$): 1.48(d, 3H), 2.28–2.67(m, 2H), 2.78–3.2(m, 2H), 3.25–3.73(m, 1H), 7.0–7.35(m, 3H).

To 15 g of 4A molecular sieves in 250 ml of dry toluene were added piperazine (6.37 g) and 6-chloro-1-methyl-2-tetralone (8.6 g). Using a Dean-Stark water trap, the mixture was stirred and heated at reflux under a nitrogen atmosphere. After 23 hours, NMR analysis of a sample of the reaction solution showed the presence of tetralone. Fifty mg of p-toluenesulfonic acid were added, and the mixture was stirred and refluxed for an additional 26 hours. An additional 10 g of 4A sieves was added, and reflux was continued for an additional 10 hours. The sieves were filtered, and toluene was evaporated from the filtrate. The residue was dissolved in a mixture of 200 ml of THF and 20 ml of methanol. To the resulting solution, stirred under nitrogen and with ice bath cooling, was added sodium cyanoborohydride (2.68 g). Gaseous HCl was added to the solution, in portions, until the solution remained acidic. After stirring overnight at room temperature, solvents were removed on a rotary evaporator, and the residue was partitioned between ether and dilute hydrochloric acid. The acidic solution was separated and made basic in the cold with sodium hydroxide. The oil which separated was extracted with ether, and the ether solution was dried ($MgSO_4$). Removal of the ether left 8.1 g of an oil. The oil was combined with 1 g of the product from a previous small scale reaction. A solution of the total in ethanol was treated with excess gaseous HCl. The crystals which separated were filtered and digested on the steam bath with 100 ml of methanol. The several crops of crystals obtained from the methanol were combined and recrystallized from ethanol to provide 6.3 g of the title compound. When dried at 120° C. in vacuo, the dihydrochloride lost one mol of hydrogen chloride and gave the following:

Analysis, calculated for $C_{15}H_{22}N_2Cl_2$: Theory: C, 59.80; H, 7.36: N. 9.30. Found: C, 59.83; H, 7.11; N, 9.29.

A sample of the dihydrochloride salt was treated with sodium hydroxide to obtain the free amine having the following analysis:

NMR ($CDCl_3$): 1.14(d, J=7, 3H), 1.63(m, J=6.4, 12, 1H), 2.06(m, J=3, 1, 1H), 2.14(broad m, 1H), 2.36(m, J=3, 4.4, 12, 1H), 2.48–2.68(m, 4H), 2.75(m, 1H), 2.85(m, 1H), 2.93 (t, J=5.2, 4H), 3.14(m, J=7, 4.4, 1, 1H), 6.97–7.12 (m, 3H).

Upon standing in a humid atmosphere for 60 hours, a sample of the dihydrochloride gave the dihydrochloride dihydrate. m.p. 244°–246° C.

Analysis, calculated for $C_{15}H_{27}N_2O_2Cl_3$: Found: C, 48.30; H, 7.05; N, 7.35.

The free amine was obtained from the (±) racemic crystalline dihydrochloride (32.7 g) with water, ether, and 40 ml of 5N NaOH. The basic aqueous portion was extracted an additional three times with ether. The combined ethereal extracts were washed twice with water and once with a saturated sodium chloride solution. The ethereal solution was dried over $MgSO_4$, filtered and evaporated to give 24.8 g of the free amine.

A. Preparation of
(+)cis-1-methyl-2-piperazinyl-6-chloro-1,2,3,4-tetrahydronaphthalene, (−)di-p-toluoyl-L-tartaric acid salt (2:1)

(−)Di-p-toluoyl-L-tartaric acid (18.9 g) dissolved in 42 ml of methanol was added to the free amine (24.8 g) in 100 ml of methanol with stirring. The precipitate was triturated ten times with hot methanol containing 10% water (total volume 11.25 l) to give 21.2 g of the (−)di-p-toluoyl-L-tartaric acid salt. m.p. 244–245° C.

The free amine was obtained from salt (21.1 g) with ether, water, and 10 ml of 5N sodium hydroxide. The combined ethereal extracts were washed four times with water and once with saturated sodium chloride. The ethereal solution was dried over MgSO$_4$, filtered, and evaporated to give 11.3 g.

(−)Di-p-toluoyl-L-tartaric acid (8.64 g) dissolved in 60 ml of methanol was added to the amine (11.3 g) in 1400 ml of methanol. The mixture was warmed briefly on a steam bath and allowed to stand at room temperature. The precipitate was filtered and washed with methanol and then with ether, and it was dried in vacuo to give 19.2 g of the (−)di-p-toluoyl-L-tartaric acid salt. m.p. 250–251° C.

Analysis, calculated for $C_{50}H_{60}N_4O_8Cl_2$: Theory: C, 65.57; H, 6.60; N, 6.12. Found: C, 65.61; H, 6.50; N, 6.15.

B. Preparation of (+)cis-1-methyl-2-piperazinyl-6-chloro-1,2,3,4-tetrahydronaphthalene, D(−)tartaric acid salt (1:1)

D(−)-tartaric acid (5.78 g) dissolved in 100 ml of methanol was added to the free amine obtained from Part A dissolved in 450 ml of methanol. A precipitate which formed quickly was allowed to stand at room temperature overnight. It was filtered and washed with methanol and then with ether. It was air dried to give 14.5 g of the D(−)-tartaric acid salt, m.p. 203° C. The D(−)-tartaric acid salt was recrystallized by dissolving it in 4.5 l of methanol containing 50 ml of water at reflux, after which the solution was concentrated to 2.5 liters.

After standing at room temperature overnight, the precipitate was filtered and washed with methanol and then with ether. Upon drying, 11.3 g of the D(−)-tartaric acid salt was obtained. m.p. 208°–209° C.

Analysis, calculated for $C_{19}H_{27}N_2O_6Cl$: Theory: C, 55.01; H, 6.56; N, 6.75. Found: C, 55.12; H, 6.71; N, 6.68.

Specific Rotation in DMSO at 25C°: @589 nm +48.04 degrees. @365 nm +176.94 degrees.

C. (+)cis-1-Methyl-2-piperazinyl-6-chloro-1,2,3,4-tetrahydronaphthalene dihydrochloride dihydrate The free base was prepared from the D(−)-tartaric acid salt using 50 ml of 1N sodium hydroxide and ether. The ether extracts were washed twice with 25 ml of 1N sodium hydroxide. These basic aqueous extracts were extracted three times with ether. The combined ethereal extracts were washed twice with water and once with saturated sodium chloride solution. The ethereal solution was dried over Na$_2$SO$_4$, filtered, and evaporated.

The dihydrochloride salt was prepared by addition of methanolic HCl to the free amine in methanol. The precipitate was filtered, washed with methanol and dried to give 7.0 g. m.p. 205° C.

Specific Rotation in water at 25° C: @589 nm +47.72 degrees. @365 nm +175.84 degrees.

A sample of the dihydrochloride salt was hydrated in a humid atmosphere for 40 hours to obtain the dihydrochloride dihydrate. m.p. 225°–230° C.

Analysis, calculated for $C_{15}H_{27}N_2O_2Cl_3$: Theory: C, 48.21; H, 7.28; N, 7.50. Found: C, 48.17; H, 7.01; N, 7.58.

Specific Rotation in water at 25° C: @589 nm +45.83 degrees. @365 nm +169.64 degrees.

D. (−)cis-1-Methyl-2-piperazinyl-6-chloro-1,2,3,4-tetrahydronaphthalene, (+)di-p-toluoyl-D-tartaric acid salt (2:1)

The combined filtrates from the triturations of (+)cis-1-methyl-2-piperazinyl-6-chloro-1,2,3,4-tetrahydronaphthalene, (−)di-p-toluoyl-L-tartaric acid salt (2:1) were combined and converted to the free amine (11.8 g) using a mixture of ether, water, and sodium hydroxide.

(+)Di-p-toluoyl-D-tartaric acid (9.0 g) dissolved in 60 ml of methanol was added to the amine in 1500 ml of methanol. The mixture was warmed briefly on a steam bath and allowed to stand at room temperature overnight.

The precipitate was filtered and washed with methanol and then with ether. After drying in vacuo, 23.5 g of the (+)di-p-toluoyl-D-tartaric acid salt were obtained. m.p. 249–250° C.

Analysis, calculated for $C_{50}H_{60}N_4O_8Cl_2$: Theory: C, 65.57; H, 6.60; N, 6.12. Found: C, 65.41; H, 6.41; N, 6.12.

E. (−)cis-1-Methyl-2-piperazinyl-6-chloro-1,2,3,4-tetrahydronaphthalene, L(+)-tartaric acid salt (1:1)

The free amine was prepared from this salt (23.5 g) with ether and 1N sodium hydroxide. The basic aqueous portion was extracted an additional three times with ether. The combined ethereal extracts were washed three times with water and once with a saturated sodium chloride solution. The ethereal solution was dried over Na$_2$SO$_4$, filtered and evaporated to give 9.7 g of the free amine.

L(+)-Tartaric acid (5.53 g) dissolved in 100 ml of methanol was added to the free amine in 500 ml of methanol. The precipitate which formed upon completion of addition of the acid was allowed to stand at room temperature overnight. The precipitate was filtered and washed with methanol and then with ether. After air drying, 14.4 g of the L(+)-tartaric acid salt were obtained. m.p. 204°–206° C.

This salt was recrystallized by dissolving it in 4.5 l of methanol at reflux after which the solution was concentrated to 2l, filtered, and allowed to stand at room temperature overnight.

The resulting precipitate was filtered and washed with methanol and then with ether. After drying, 11.1 g of the L(+)-tartaric acid salt were obtained. m.p. 208°–209° C.

Analysis, calculated for $C_{19}H_{27}N_2O_6Cl$: Theory: C, 55.01; H, 6.56; N, 6.75. Found: C, 55.18; H, 6.79; N, 6.76.

Specific Rotation in DMSO at 25° C: @589 nm −45.57 degrees. @365 nm −169.75 degrees.

F. (−)cis-1-Methyl-2-piperazinyl-6-chloro-1,2,3,4-tetrahydronaphthalene dihydrochloride dihydrate The free amine of the product from Part E (11.1 g) was prepared by treating it with 55 ml of 1N sodium hydroxide and ether. The ether extract was washed twice with 25 ml of 1N sodium hydroxide. The combined basic aqueous portions were extracted three times with ether. The combined ethereal extracts were washed twice with 25 ml of water and once with a saturated sodium chloride solution. The ethereal solution was dried over sodium sulfate, filtered and evaporated.

The dihydrochloride salt was obtained by the addition of methanolic HCl to the free amine in methanol. The resulting precipitate was filtered and washed with methanol to give 7.5 g. m.p. 216°–218° C. Specific Rotation in water at 25° C: −589 nm −44.73 degrees. @365 nm −166.11 degrees.

A sample of the dihydrochloride salt was hydrated to the dihydrate by allowing it to stand in a humid atmosphere for 40 hours to obtain 7.5 g. m.p. 230°–235° C.

Analysis, calculated for $C_{15}H_{27}N_2O_2Cl_3$: Theory: C, 48.21; H, 7.28; N, 7.50. Found: C, 48.20; H, 7.07; N, 7.56.

Specific Rotation in water at 25° C: @589 nm −45.68 degrees. @365 nm −167.63 degrees.

EXAMPLE 34

Preparation of
1-Methyl-2-piperazinyl-1,2,3,4-tetrahydronaphthalene dihydrochloride Using 1-methyl-2-tetralone and piperazine in the method as described in Example 33, the title compound was obtained. m.p. 227°–230° C. (ethanol).

Analysis, calculated for $C_{15}H_{24}N_2Cl_2$: Theory: C, 59.41; H, 7.98; N, 9.24. Found: C, 59.37; H, 7.73; N, 9.52.

EXAMPLE 35

Preparation of
1-Methyl-2-(N-methylpiperazinyl-1,2,3,4-tetrahydronaphthalene dihydrochloride A solution of 1-methyl-2-tetralone (5.0 g), and N-methylpiperazine (6.25 g), in 140 ml of toluene was stirred and refluxed under a nitrogen atmosphere utilizing a Dean-Stark trap for azeotropic removal of water. After 60 hours, the toluene was evaporated, and the residue was dissolved in 90 ml of THF and 9 ml of methanol. The solution was cooled with stirring under nitrogen, 2.0 g of sodium cyanoborohydride were added, and gaseous HCl was added portionwise periodically as required until the solution remained acidic. Workup, isolation and treatment of the crude basic product with dry HCl as described in Example 33 provided the title compound. m.p. 262°–265° C. dec. (ethanol).

Analysis calculated for $C_{16}H_{26}N_2Cl_2$: Theory: C, 60.57; H, 8.26; N, 8.83. Found: C, 60.84; H, 8.10; N, 8.96.

EXAMPLE 36

Preparation of
2-Homopiperazinyl-6-chloro-1,2,3,4-tetrahydronaphthalene dihydrochloride To a solution of 6-chloro-2-tetralone (7.22 g) and homopiperazine (8.0 g) in 100 ml of toluene were added 10 g of 3A molecular sieves. The mixture was heated on the steam bath for 2 hours, the sieves were filtered off, and toluene was evaporated from the filtrate. The residue was dissolved in a mixture of 100 ml of THF and 30 ml of methanol. The resultant solution was cooled in an ice bath with stirring under nitrogen, 2.51 g of sodium cyanoborohydride were added, and, with stirring and cooling, gaseous HCl was added portionwise periodically until the solution remained acidic. After stirring overnight at room temperature, the solvents were evaporated, and the residue was partitioned between dilute hydrochloric acid and ether. The acidic aqueous layer was separated and made basic with sodium hydroxide. The oil which formed was extracted with ether. The ether solution was dried ($MgSO_4$), and the ether was evaporated. The residue was dissolved in ethanol, and excess gaseous HCl was added to the solution The solvent was evaporated. The residue crystallized slowly from a mixture of ethanol and ether to obtain 3.22 g of the title compound. m.p. 181°–183° C.

Analysis, calculated for $C_{15}H_{23}N_2Cl_3$: Theory: C, 53.35; H, 6.86; N, 8.29. Found: C, 53.40; H, 7.12; N, 8.49.

EXAMPLE 37

Preparation of
2-Piperazinyl-6-hydroxy-1,2,3,4-tetrahydronapthalene dihydrobromide The product from Example 29 (0.30 g) and 48% hydrobromic acid (12 ml) were warmed for 3 hours and heated at reflux with stirring under nitrogen for 2.5 hours. The reaction mixture was evaporated to dryness, and the residue, in ethanol, was heated on a steam bath. After standing at room temperature for two days, the mixture was filtered, and the solid was dried to obtain 0.37 g of the title compound, m.p. 192°–194° C.

Analysis, calculated for $C-H>N_2OBr_2$: Theory: C, 42.66; H, 5.63; N, 7.11. Found: C, 42.53; H, 5.53; N, 6.95.

EXAMPLE 38

Preparation of
2-(N-Methylpiperazinyl)-5-difluoromethyl-8-methoxy-1,2,3,4-tetrahydronaphthalene dimaleate To 3 ml of methylene chloride was added 0.43 g (1.49 mmole) of 2-(N-methylpiperazinyl)-5-formyl-8-methoxy-1,2,3,4-tetrahydronaphthalene. To the solution then were added 4.0 ml of DAST, and the mixture was stirred for 18 hours at room temperature. The mixture then was poured cautiously over ice, made basic with ammonium hydroxide, and extracted well with ether. The organics were combined, dried over $Na_2SO_4$, and evaporated in vacuo to give 0.31 g of a yellow, viscous oil.

The oil was dissolved in methylene chloride, and the solution was placed on a flash silica column. The column was eluted with methylene chloride containing 3% methanol and a trace of ammonium hydroxide to give 0.12 g of a light yellow, viscous oil.

The oil was dissolved in hot ethanol. To the solution were added 2.1 equivalents of maleic acid. Crystals formed as heating was continued. The mixture was cooled to room temperature, and 0.12 g of the title compound was recovered by filtration. m.p. 189°–189.5° C.

Analysis, calculated for $C_{17}H_{24}N_2OF_2 \cdot 2C_4H_4O_4$: Theory: C, 55.35; H, 5.95; N, 5.16. Found: C, 55.57; H, 5.99; N, 5.17.

NMR ($CDCl_3$): 7.28–7.08(d, J=9Hz, 1H), 6.68–6.46 (d, J=9Hz, 1H), 7.20–5.92 (t, J=55.8 Hz, 1H), 3.80 (s, 3H), 3.2–2.0 (m, 14H), 2.30 (s, 3H), 1.8–1.3 (m, 1H).

MS: 311 (10), 310 (58), 309 (6), 291 (5), 290 (15), 282 (4), 266 (10), 248 (3), 247 (12), 246 (7), 240 (7), 239 (29), 238 (10), 211 (30), 210 (28), 191 (12), 160 (15), 159 (20), 100 (100), 99 (25), 70 (41), 58 (70).

EXAMPLE 39

Preparation of
2-(N-Methylpiperizinyl)-6-methylthio-1,2,3,4-tetrahydronaph

At −60° C. with stirring, 3.3 ml of n-butyllithium (1.52 N) was added to 1.15 g of the free base from Example 31 dissolved in dry tetrahydrofuran (THF). The solution was stirred at −60° C. for 15 minutes, and 0.71 g dimethyl disulfide in 4 ml of THF was added with stirring. The reaction mixture was stirred for 10 minutes at −60° C. and then was permitted to warm to room temperature with stirring for two hours.

The reaction mixture was evaporated, and the residue was dissolved in ether. The ethereal solution was washed three times with saturated aqueous sodium chloride, dried over MgSO$_4$, filtered, and evaporated. The crystalline dihydrochloride was made from the residue in ethanol with the addition of ethanolic HCl. Filtration gave 0.77 g. of the title compound. m.p. 245°–248° C. (ethanol).

Analysis, calculated for $C_{16}H_{26}N_2SCl_2$: Theory: C, 55.01; H, 7.50; N; 8.02. Found: C, 55.25; H, 7.70; N, 7.82.

EXAMPLE 40

Preparation of
1-Methyl-2-piperazinyl-6-bromo-1,2,3,4-tetrahydronaphthalene dihydrochloride Four grams of 1-methyl-6-bromo-1,2,3,4-tetrahydronaphthalen-2-one and 2.89 g of piperazine were heated at reflux overnight in 100 ml of toluene containing 5 g of 4A molecular sieves and 50 mg of p-toluenesulfonic acid. The reaction mixture was filtered, and the filtrate was evaporated. Sodium cyanoborohydride (1.05 g), 100 ml of THF, and 10 ml of methanol were added to the residue. Gaseous HCl was added periodically above the solution with stirring at ice bath temperatures until the solution remained acidic.

The reaction mixture was stirred at room temperature overnight and evaporated. The residue was extracted with ether and water. The acidic aqueous portion was made alkaline in the cold with sodium hydroxide and extracted with ether. The ether extract was dried over MgSO$_4$, filtered, and evaporated to give an oil. The dihydrochloride salt was prepared by addition of gaseous HCl to the free base in ethanol in the cold. Recrystallization of the dihydrochloride salt from methanol gave 0.45 g of the title compound. m.p. 243°–245° C.

Analysis, calculated for $C_{15}H_{23}N_2BrCl_2$: Theory: C, 47.14; H, 6.07; N, 7.33. Found: C, 47.39; H, 6.31; N, 7.15.

As noted above, the compounds of this invention are useful for selectively inhibiting the reuptake of serotonin. Therefore, another embodiment of the present invention is a method for inhibiting serotonin reuptake in mammals which comprises administering to a mammal requiring increased neurotransmission of serotonin a pharmaceutically effective amount of a compound of the invention.

The term "pharmaceutically effective amount", as used herein, represents an amount of a compound of the invention which is capable of inhibiting serotonin reuptake. The specific dose of compound administered according to this invention will, of course, be determined by the particular circumstances surrounding the case, including, for example, the compound administered, the route of administration, and the condition being treated. A typical daily dose generally will contain from about 0.01 mg/kg to about 20 mg/kg of the active compound of this invention. Preferred daily doses generally will be from about 0.05 to about 10 mg/kg, and ideally from about 0.1 to about 5 mg/kg.

The compounds can be administered by a variety of routes including oral, rectal, transdermal, subcutaneous, intravenous, intramuscular, and intranasal. A special feature of the compounds of this invention is that they have a prolonged duration of action and therefore are capable of inhibiting the reuptake of serotonin for an extended period of time. It is also a special feature of the compounds of this invention that they have been found to demonstrate a low degree of toxicity to mammals. Finally, the compounds of the invention are extremely selective as inhibitors of serotonin reuptake relative to the reuptake of other monoamines.

A variety of physiologic functions have been shown to be subject to influence by brain serotonergic neural systems. As such, the compounds of this invention are believed to have the ability to treat in mammals a variety of disorders associated with these neural systems such as eating disorders, depression, alcoholism, pain, loss of memory, anxiety, and smoking. Therefore, the present invention also provides methods of treating the above disorders at rates set forth above for inhibiting serotonin reuptake in mammals.

The following experiment was conducted to demonstrate the ability of the compounds of the present invention to inhibit the reuptake of serotonin. This general procedure is set forth in Wong et al., Drug *Development Research* 6%397–403 (1985).

Male Sprague-Dawley rats (110–150 g) from Harlan Industries (Cumberland, IN) were fed Purina Chow ad libitum for at least 3 days before being used in the studies. Rats were killed by decaptiation. Whole brains were removed and dissected. Cerebral cortex was homogenized in 9 volumes of a medium containing 0.32 M sucrose and 10 mM glucose. Crude synaptosomal preparations were isolated after differential centrifugation at 1,000 g for 10 min. and 17,000 g for 28 min. The final pellets were suspended in the same medium and kept in ice until use within the same day.

Synaptosomal uptake of $^3$H-serotonin ($^3$H-5-hydroxytryptamine, $^3$H-5HT) was determined as follows: Cortical synaptosomes (equivalent to 1 mg of protein) were incubated at 37° C. for 5 min in 1 ml of Krebsbicarbonate medium containing also 10 mM glucose, 0.1 iproniazid, 1 mM ascorbic acid, 0.17 mM EDTA and 50 nM $^3$H-5HT. The reaction mixture was immediately diluted with 2 ml of ice-chilled Krebs-bicarbonate buffer and filtered under vacuum with a cell harvester (Brandel, Gaithersburg, MD). Filters were rinsed twice with approximately 5 ml of ice-chilled 0.9% saline and were transferred to a counting vial containing 10 ml of scintillation fluid (PCS, Amersham, Arlington Heights, IL). Radioactivity was measured by a liquid scintillation spectrophotometer Accumulation of $^3$H-5HT at 4° C. represented the background and was subtracted from all samples.

The results of the evaluation of various compounds of the present invention are set forth below in Table I. In Table I, the first column provides the Example Number of the compound evaluated; the next 7 columns identify the structure of the compound evaluated when taken with the formula set forth in the heading; the next-succeeding column identifies the salt form of the compound evaluated; and the final column provides the amount of the test compound expressed in nanomolar concentration needed to inhibit the uptake of $^3$H-5HT by 50%, and is indicated in Table I as $IC_{50}$. Numbers in parentheses, if any, represent percent inhibition at 1000 nM.

TABLE I

INHIBITION OF 5HT UPTAKE IN VITRO

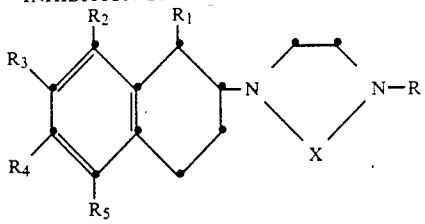

| Compound of Example No. | R | R₁ | R₂ | R₃ | R₄ | R₅ | X | Salt Form | IC₅₀(nM) 5HT |
|---|---|---|---|---|---|---|---|---|---|
| 1 | CH₃ | H | OCH₃ | H | H | H | (CH₂)₂ | dihydrochloride | 57 |
| 2 | H | H | OCH₃ | H | H | H | (CH₂)₂ | dihydrochloride | 90 |
| 3 | H | H | Cl | H | H | H | (CH₂)₂ | dimaleate | 83 |
| 4 | CH₃ | H | Cl | H | H | H | (CH₂)₂ | dimaleate | 35 |
| 5 | H | H | Cl | H | H | H | (CH₂)₃ | dimaleate | 260 |
| 6 | CH₃ | H | F | H | H | H | (CH₂)₂ | dimaleate | 180 |
| 7 | CH₃ | H | CH₃ | H | H | H | (CH₂)₂ | dihydrochloride | 87 |
| 8 | CH₃ | H | CH₃ | H | H | CH₃ | (CH₂)₂ | dihydrochloride | 140 |
| 9 | CH₃ | H | Br | H | H | H | (CH₂)₂ | dimaleate | 90 |
| 10 | CH₃ | H | OCH₃ | H | H | OCH₃ | (CH₂)₂ | dihydrochloride | 100 |
| 11 | CH₃ | CH₃ | Cl | H | H | H | (CH₂)₂ | dimaleate | 650 |
| 12 | H | CH₃ | Cl | H | H | H | (CH₂)₂ | dihydrobromide | 270 |
| 14 | CH₃ | H | OH | H | H | H | (CH₂)₂ | dihydrobromide | 50 |
| 15 | CH₃ | H | OCH₃ | H | H | Br | (CH₂)₂ | dihydrochloride | 12 |
| 16 | H | H | OCH₃ | H | H | Br | (CH₂)₂ | dihydrochloride | 3.7 |
| 17 | CH₃ | H | CH₃ | H | H | Br | (CH₂)₂ | dihydrochloride | 17 |
| 18 | CH₃ | H | SCH₃ | H | H | H | (CH₂)₂ | dimaleate | 40 |
| 19 | H | CH₃ | OCH₃ | H | H | Br | (CH₂)₂ | dihydrochloride | 70 |
| 20 | CH₃ | H | OCH₃ | H | H | F | (CH₂)₂ | dimaleate | 60 |
| 21 | CH₃ | H | OCH₃ | H | H | Cl | (CH₂)₂ | dihydrochloride | 16 |
| 22 | CH₃ | H | OCH₃ | H | H | I | (CH₂)₂ | dihydrochloride | 23 |
| 23 | CH₃ | H | OCH₃ | H | H | CHO | (CH₂)₂ | dihydrochloride | 10 |
| 24 | CH₃ | H | OCH₃ | H | H | CN | (CH₂)₂ | dihydrochloride | 12 |
| 25 | H | H | H | H | Cl | H | (CH₂)₂ | dihydrochloride | 100 |
| 26 | H | H | H | H | Br | H | (CH₂)₂ | dihydrochloride | 350 |
| 27 | H | H | H | H | F | H | (CH₂)₂ | dihydrochloride | 340 |
| 28 | H | H | H | H | CH₃ | H | (CH₂)₂ | dihydrochloride | 210 |
| 29 | H | H | H | H | OCH₃ | H | (CH₂)₂ | dihydrochloride | 750 |
| 30 | H | H | H | Cl | Cl | H | (CH₂)₂ | dihydrochloride | 115 |
| 31 | CH₃ | H | H | H | Br | H | (CH₂)₂ | dihydrochloride | 520 |
| 32 | CH₃ | H | H | H | Cl | H | (CH₂)₂ | dihydrochloride | 450 |
| 33 | H | CH₃ (Racemate) | H | H | Cl | H | (CH₂)₂ | dihydrochloride | 12 |
| 33a | H | CH₃ (+enantiomer) | H | H | Cl | H | (CH₂)₂ | dihydrochloride | 84 |
| 33b | H | CH₃ (+enantiomer) | H | H | Cl | H | (CH₂)₂ | dihydrochloride | 8.2 |
| 34 | H | CH₃ | H | H | H | H | (CH₂)₂ | dihydrochloride | 59 |
| 35 | CH₃ | CH₃ | H | H | H | H | (CH₂)₂ | dihydrochloride | 490 |
| 36 | H | H | H | H | Cl | H | (CH₂)₃ | dihydrochloride | 240 |
| 37 | H | H | H | H | OH | H | (CH₂)₂ | dihydrobromide | 1000 |
| 38 | CH₃ | H | OCH₃ | H | H | CF₂H | (CH₂)₂ | dimaleate | 23 |
| 39 | CH₃ | H | H | H | SCH₃ | H | (CH₂)₂ | dihydrochloride | 434 |
| 40 | H | CH₃ | H | H | Br | H | (CH₂)₂ | dihydrochloride | 34 |

The compounds of this invention are preferably formulated prior to administration. Therefore, another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsuleS, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methylhydroxybenzoates, propyl hydroxybenzoates, talc, magnesium stearate, and mineral oil. The formulations may additionally include lubricating agents, wetting agents, emulsifying agents, suspending agents, preserving agents, sweetening agents, flavoring agents, and the like. The compositions of the invention may be formulated so as to provide quick, sustained or delayed release of the active ingredient after administration to the patient by employing procedures well known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

|  | Quantity (mg/capsule) |
|---|---|
| cis-1-methyl-2-piperazinyl-6-chloro-1,2,3,4-tetrahydronaphthalene dihydrochloride dihydrate | 250 |
| starch, dried | 200 |
| magnesium stearate | 10 |
| Total | 460 mg |

The above ingredients are mixed and filled into hard gelatin capsules in 460 mg quantities.

FORMULATION 2

A tablet is prepared using the ingredients below:

|  | Quantity (mg/tablet) |
|---|---|
| cis-1-methyl-2-piperazinyl-1,2,3,4-tetrahydronaphthalene dihydrochloride | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

An aerosol solution is prepared containing the following components:

|  | Weight % |
|---|---|
| 2-piperazinyl-6-chloro-1,2,3,4-tetrahydronaphthalene dihydrochloride | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

|  |  |
|---|---|
| 2-(N-methylpiperazinyl)-8-chloro-1,2,3,4-tetrahydronaphthalene dimaleate | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

|  |  |
|---|---|
| 2-piperazinyl-5-bromo-8-methoxy-1,2,3,4-tetrahydronaphthalene dihydrochloride | 80 mg |
| starch | 59 mg |
| microcrystalline cellulose | 59 mg |
| magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

|  |  |
|---|---|
| 2-(N-methylpiperazinyl)-5-formyl-8-methoxy-1,2,3,4-tetrahydronaphthalene dihydrochloride hydrate | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is them poured into a suppository mold of nominal 2 g capacity and allowed to cool.

FORMULATION 7

Suspensions, each containing 50 mg of active ingredient per 5 ml dose, are made as follows:

|  |  |
|---|---|
| 2-(N-methylpiperazinyl)-5-cyano-8-methoxy- | 50 mg |

| | |
|---|---|
| 1,2,3,4-tetrahydronaphthalene dihydrochloride | |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| | |
|---|---|
| 2-(N-methylpiperazinyl)-8-methoxy-1,2,3,4-tetrahydronaphthalene dihydrochloride | 100 mg |
| isotonic saline | 1000 ml |

The solution of the above ingredients generally is administered intravenously at a rate of 1 ml per minute to a subject suffering from depression.

We claim:

1. A compound of the formula

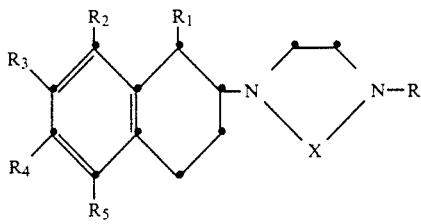

in which

R is hydrogen or methyl; $R_1$ is hydrogen or methyl; X is $-CH_2CH_2-$ or $-CH_2CH_2CH_2-$;

$R_2$ is selected from the group consisting of hydrogen, halo, $C_1$-$C_3$ alkoxy, $C_1$-$C_3$ thioalkyl, $C_1$-$C_3$ alkyl, and hydroxy:

$R_3$ is selected from the group consisting of hydrogen and halo;

$R_4$ is selected from the group consisting of hydrogen, halo, $C_1$-$C_3$ alkyl, and $C_1$-$C_3$ thioalkyl;

$R_5$ is selected from the group consisting of hydrogen, halo, $C_1$-$C_3$ alkyl, $C_1$-$C_3$ acyl, fluorosubstituted $C_2$-$C_3$ acyl, fluoro-substituted $C_1$-$C_3$ alkyl, cyano, carboxamido, carboxyl, and $C_1$-$C_3$ hydroxyalkyl;

all subject to the following provisos;

(a) if $R_1$ is methyl, both $R_2$ and $R_4$ may be hydrogen;

(b) if $R_1$ is hydrogen, one of $R_2$ and $R_4$ is hydrogen and the other is other than hydrogen;

(c) $R_5$ may be other than hydrogen only when $R_2$ is other than hydrogen;

(d) when $R_2$ is other than hydrogen, $R_5$ also is other than hydrogen; and (e) $R_3$ may be halo only when $R_4$ is other than hydrogen;

or pharmaceutically acceptable acid addition salts thereof.

2. Compound of claim 1, in which $R_5$ is selected from the group consisting of hydrogen, halo, $C_1$-$C_3$ alkyl, $C_1$-$C_3$ acyl, fluorosubstituted $C_2$-$C_3$ acyl, fluoro-substituted $C_1$-$C_3$ alkyl, and cyano.

3. Compound of claim 2, in which $R_2$ is selected from the group consisting of halo, $C_1$-$C_3$ alkoxy, thioalkyl, $C_1$-$C_3$ alkyl, and hydroxy.

4. Compound of claim 3, in which X is $-CH_2CH_2-$.

5. Compound of claim 4, in which $R_1$ is hydrogen.

6. Compound of claim 5, in which R is methyl.

7. Compound of claim 5, in which $R_2$ is $C_1$-$C_3$ alkoxy or halo.

8. Compound of claim 7, in which $R_2$ is halo.

9. Compound of claim 8, in which $R_2$ is chloro.

10. Compound of claim 7, in which $R_2$ is $C_1$-$C_3$ alkoxy.

11. Compound of claim 10, in which $R_2$ is methoxy.

12. Compound of claim 1, in which $R_5$ is halo.

13. Compound of claim 12, in which $R_5$ is bromo.

14. Compound of claim 2, $R_4$ is selected from the group consisting of halo, $C_1$-$C_3$ alkyl, and $C_1$-$C_3$ thioalkyl.

15. Compound of claim 14, in which X is $-CH_2CH_2-$.

16. Compound of claim 15 in which $R_1$ is methyl.

17. Compound of claim 16 in which R is hydrogen.

18. Compound of claim 17 in which $R_4$ is halo.

19. Compound of claim 18 in which $R_4$ is chloro.

20. Compound of claim 19, in which $R_3$ is hydrogen.

21. A method for inhibiting serotonin reuptake in mammals which comprises administering to a mammal requiring increased neurotransmission of serotonin a pharmaceutically effective amount of a compound of the formula

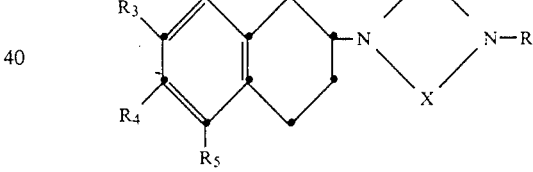

in which

R is hydrogen or methyl; $R_1$ is hydrogen or methyl; X is $-CH_2CH_2-$ or $-CH_2CH_2CH_2-$ $R_2$ is selected from the group consisting of hydrogen, halo, $C_1$-$C_3$ alkoxy, $C_1$-$C_3$ thioalkyl, $C_1$-$C_3$ alkyl, and hydroxy;

$R_3$ is selected from the group consisting of hydrogen and halo;

$R_4$ is selected from the group consisting of hydrogen, halo, $C_1$-$C_3$ alkyl, $C_1$-$C_3$ alkoxy, $C_1$-$C_3$ thioalkyl, and hydroxy;

$R_5$ is selected from the group consisting of hydrogen, halo, $C_1$-$C_3$ alkyl, $C_1$-$C_3$ alkoxy, $C_1$-$C_3$ acyl, fluorosubstituted $C_2$-$C_3$ acyl, fluoro-substituted $C_1$-$C_3$ alkyl, and cyano;

all subject to the following provisos:

(a) if $R_1$ is methyl, both $R_2$ and $R_4$ may be hydrogen;

(b) if $R_1$ is hydrogen, one of $R_2$ and $R_4$ is hydrogen and the other is other than hydrogen;

(c) $R_2$ may be other than hydrogen only when $R_2$ is other than hydrogen; and (d) $R_3$ may be halo only when $R_4$ is other than hydrogen;

and pharmaceutically acceptable acid addition salts thereof.

22. Method of claim 21, in which the compound is 1-methyl-2-piperazinyl-6-chloro-1,2,3,4-tetrahydronaphthalene or a pharmaceutically acceptable acid addition salt thereof.

23. A method of treating depression in humans comprising administering to a human suffering from depression an effective antidepressant dose of a compound of the formula

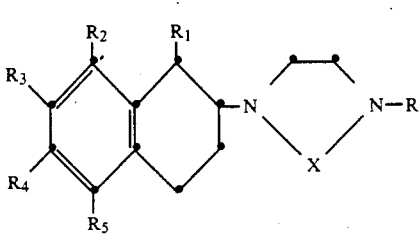

in which
R is hydrogen or methyl; $R_1$ is hydrogen or methyl; X is $-CH_2CH_2-$ or $-CH_2CH_2CH_2-$;
$R_2$ is selected from the group consisting of hydrogen, halo, $C_1-C_3$ alkoxy, $C_1-C_3$ thioalkyl, $C_1-C_3$ alkyl, and hydroxy;
$R_3$ is selected from the group consisting of hydrogen and halo;
$R_4$ is selected from the group consisting of hydrogen, halo, $C_1-C_3$ alkyl, $C_1-C_3$ alkoxy, $C_1-C_3$ thioalkyl, and hydroxy;
$R_5$ is selected from the group consisting of hydrogen, halo, $C_1-C_3$ alkyl, $C_1-C_3$ alkoxy, $C_1-C_3$ acyl, fluorosubstituted $C_2-C_3$ acyl, fluoro-substituted $C_1-C_3$ alkyl, and cyano;
all subject to the following provisos:
 (a) one of $R_2$ and $R_4$ is hydrogen and the other is other than hydrogen;
 (b) R may be other than hydrogen only when $R_2$ is other than hydrogen; and
 (c) $R_2$ may be halo only when $R_4$ is other than hydrogen;
and pharmaceutically acceptable acid addition salts thereof.

24. Method of claim 23, in which the compound is 1-methyl-2-piperazinyl-6-chloro-1,2,3,4-tetrahydronaphthalene or a pharmaceutically acceptable acid addition salt thereof.

25. A method of treating anxiety in humans comprising administering to a human suffering from anxiety an effective antianxiety dose of a compound of the formula

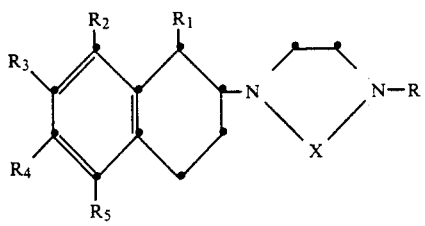

in which
R is hydrogen or methyl; $R_1$ is hydrogen or methyl; X is $-CH_2CH_2-$ or $-CH_2CH_2CH_2-$;
$R_2$ is selected from the group consisting of hydrogen, halo, $C_1-C_3$ alkoxy, $C_1-C_3$ thioalkyl, and hydroxy;
$R_3$ is selected from the group consisting of hydrogen and halo;
$R_4$ is selected from the group consisting of hydrogen, halo, $C_1-C_3$ alkyl, $C_1-C_3$ alkoxy, thioalkyl, and hydroxy;
$R_5$ is selected from the group consisting of hydrogen, halo, $C_1-C_3$ alkyl, $C_1-C_3$ alkoxy, $C_1-C_3$ acyl, fluorosubstituted $C_2-C_3$ acyl, fluoro-substituted $C_1-C_3$ alkyl, and cyano;
(a) one of $R_2$ and $R_4$ is hydrogen and the other is other than hydrogen;
(b) $R_5$ may be other than hydrogen only when $R_2$ is other than hydrogen; and
(c) $R_3$ may be halo only when $R_4$ is other than hydrogen;
and pharmaceutically acceptable acid addition salts thereof.

26. Method of claim 25, in which the compound is 1-methyl-2-piperazinyl-6-chloro-1,2,3,4-tetrahydronaphthalene or a pharmaceutically acceptable acid addition salt thereof.

27. A method of treating obesity in humans comprising administering to a human suffering from obesity an effective antiobesity dose of a compound of the formula

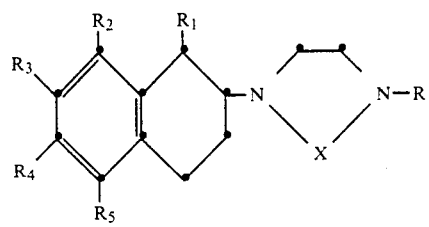

in which
R is hydrogen or methyl; $R_1$ is hydrogen or methyl; X is $-CH_2CH_2-$ or $-CH_2CH_2CH_2-$;
$R_2$ is selected from the group consisting of hydrogen, halo, $C_1-C_3$ alkoxy, $C_1-C_3$ thioalkyl, $C_1-C_3$ alkyl, and hydroxy;
$R_3$ is selected from the group consisting of hydrogen and halo;
$R_4$ is selected from the group consisting of hydrogen, halo, $C_1-C_3$ alkyl, $C_1-C_3$ alkoxy, $C_1-C_3$ thioalkyl, and hydroxy;
$R_5$ is selected from the group consisting of hydrogen, halo, $C_1-C_3$ alkyl, $C_1-C_3$ alkoxy, $C_1-C_3$ acyl, fluorosubstituted $C_2-C_3$ acyl, fluoro-substituted $C_1-C_3$ alkyl, and cyano;
all subject to the following provisos:
 (a) if $R_1$ is methyl, both $R_2$ and $R_4$ may be hydrogen;
 (b) if R is hydrogen, one of $R_2$ and $R_4$ is hydrogen and the other is other than hydrogen;
 (c) $R_5$ may be other than hydrogen only when $R_2$ is other than hydrogen; and
 (d) $R_3$ may be halo only when $R_4$ is other than hydrogen;
and pharmaceutically acceptable acid addition salts thereof.

28. Method of claim 27, in which the compound is 1-methyl-2-piperazinyl-6-chloro-1,2,3,4-tetrahydronaphthalene or a pharmaceutically acceptable acid addition salt thereof.

29. A method of suppressing the desire of humans to smoke comprising administering to a human in need of such suppression an effective dose to relieve the desire to smoke of a compound of the formula

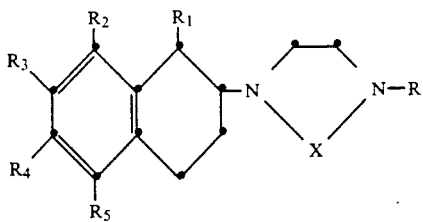

in which
R is hydrogen or methyl; $R_1$ is hydrogen or methyl; X is $-CH_2CH_2-$ or $-CH_2CH_2CH_2-$;
  $R_2$ is selected from the group consisting of hydrogen, halo, $C_1-C_3$ alkoxy, $C_1-C_3$ thioalkyl, $C_1-C_3$ alkyl, and hydroxy;
  $R_3$ is selected from the group consisting of hydrogen and halo;
  $R_4$ is selected from the group consisting of hydrogen, halo, $C_1-C_{13}$ alkyl, $C_1-C_3$ alkoxy, $C_1-C_3$ thioalkyl, and hydroxy;
  $R_5$ is selected from the group consisting of hydrogen, halo, $C_1-C_3$ alkyl, $C_1-C_3$ alkoxy, $C_1-C_3$ acyl, fluorosubstituted $C_2-C_3$ acyl, fluoro-substituted $C_1-C_3$ alkyl, and cyano;
all subject to the following provisos:
  (a) if $R_1$ is methyl, both $R_2$ and $R_4$ may be hydrogen;
  (b) if $R_1$ is hydrogen, one of $R_2$ and $R_4$ is hydrogen and the other is other than hydrogen;
  (c) $R_5$ may be other than hydrogen only when $R_2$ is other than hydrogen; and
  (d) $R_3$ may be halo only when $R_4$ is other than hydrogen;
and pharmaceutically acceptable acid addition salts thereof.

30. Method of claim 29, in which the compound is 1-methYl-2-piperazinyl-6-chloro-1,2,3,4-tetrahydronaphthalene or a pharmaceutically acceptable acid addition salt thereof.

31. A method of suppressing the desire of humans to consume alcohol comprising administering to a human in need of such suppression an effective dose to relieve the desire to consume alcohol of a compound of the formula

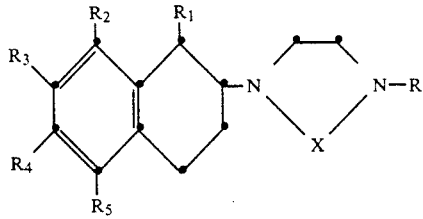

in which
  R is hydrogen or methyl;
  $R_1$ is hydrogen or methyl; X is $-CH_2CH_2-$ or $-CH_2CH_2CH_2-$;
  $R_2$ is selected from the group consisting of hydrogen, halo, $C_1-C_3$ alkoxy, $C_1-C_3$ thioalkyl, $C_1-C_3$ alkyl, and hydroxy;
  $R_3$ is selected from the group consisting of hydrogen and halo;
  $R_4$ is selected from the group consisting of hydrogen, halo, $C_1-C_3$ alkyl, $C_1-C_3$ alkoxy, $C_1-C_3$ thioalkyl, and hydroxy;
  $R_5$ is selected from the group consisting of hydrogen, halo, $C_1-C_3$ alkyl, $C_1-C_3$ alkoxy, $C_1-C_3$ acyl, fluorosubstituted $C_2-C_3$ acyl, fluoro-substituted $C_1C_3$ alkyl, and cyano;
all subject to the following provisos:
  (a) if $R_1$ is methyl, both $R_2$ and $R_4$ may be hydrogen;
  (b) if $R_1$ is hydrogen, one of $R_2$ and $R_4$ is hydrogen and the other is other than hydrogen;
  (c) $R_5$ may be other than hydrogen only when $R_2$ is other than hydrogen; and
  (d) $R_3$ may be halo only when $R_4$ is other than hydrogen;
and pharmaceutically acceptable acid addition salts thereof.

32. Method of claim 31, in which the compound is 1-methyl-2-piperazinyl-6-chloro-1,2,3,4-tetrahydronaphthalene or a pharmaceutically acceptable acid addition salt thereof.

33. A method of suppressing pain in mammals which comprises administering to a mammal in need of such suppression an effective dose to suppress such pain of a compound of the formula

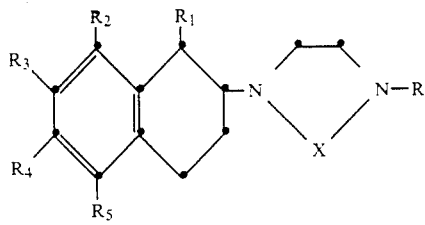

in which
  R is hydrogen or methyl; $R_1$ is hydrogen or methyl; X is $-CH_2CH_2-$ or $-CH_2CH_2CH_2-$;
  $R_2$ is selected from the group consisting of hydrogen, halo, $C_1-C_3$ a alkoxy, $C_1-C_3$ thioalkyl, alkyl, and hydroxy;
  $R_3$ is selected from the group consisting of hydrogen and halo;
  $R_4$ is selected from the group consisting of hydrogen, halo, $C_1-C_3$ alkyl, $C_1-C_3$ alkoxy, $C_1-C_3$ thioalkyl, and hydroxy;
  $R_5$ is selected from the group consisting of hydrogen, halo, $C_1-C_3$ alkyl, $C_1-C_3$ alkoxy, $C_1-C_3$ acyl, fluorosubstituted $C_2-C_3$ acyl, fluoro-substituted $C_1-C_3$ alkyl, and cyano;
all subject to the following provisos:
  (a) if $R_1$ is methyl, both $R_2$ and $R_4$ may be hydrogen;
  (b) if $R_1$ is hydrogen, one of $R_2$ and $R_4$ is hydrogen and the other is other than hydrogen;
  (c) $R_5$ may be other than hydrogen only when $R_2$ is other than hydrogen; and
  (d) $R_3$ may be halo only when $R_4$ is other than hydrogen;
and pharmaceutically acceptable acid addition salts thereof.

34. Method of claim 33, in which the compound is 1-methyl-2-piperazinyl-6-chloro-1,2,3,4-tetrahydronaphthalene or a pharmaceutically acceptable acid addition salt thereof.

35. A pharmaceutical formulation which comprises, in association with a pharmaceutically acceptable carrier, diluent, or excipient, a compound of the formula

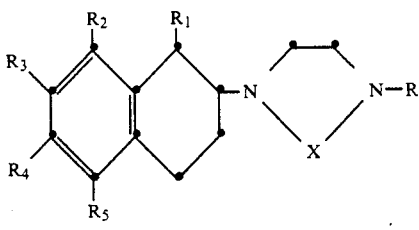

in which

R is hydrogen or methyl; $R_1$ is hydrogen or methyl; X is $-CH_2CH_2-$ or $-CH_2CH_2CH_2-$;

$R_2$ is selected from the group consisting of hydrogen, halo, $C_1-C_3$ alkoxy, $C_1-C_3$ thioalkyl, $C_1-C_3$ alkyl, and hydroxy;

$R_3$ is selected from the group consisting of hydrogen, halo, $C_1-C_3$ a alkyl, $C_1-C_3$ alkoxy, $C_1-C_3$ thioalkyl, and hydroxy;

$R_5$ is selected from the group consisting of hydrogen, halo, $C_1-C_3$ a alkyl, $C_1-C_3$ alkoxy, $C_1-C_3$ acyl, fluorosubstituted $C_2-C_3$ acyl, fluoro-substituted $C_1-C_3$ alkyl, and cyano;

all subject to the following provisos:
  (a) if $R_1$ is methyl, both $R_2$ and $R_4$ may be hydrogen;
  (b) if $R_1$ is hydrogen, one of $R_2$ and $R_4$ is hydrogen and the other is other than hydrogen;
  (c) $R_5$ may be other than hydrogen only when $R_2$ is other than hydrogen; and
  (d) $R_3$ may be halo only when $R_4$ is other than hydrogen;

and pharmaceutically acceptable acid addition salts thereof.

36. Formulation of claim 35, in which the compound is 1-methyl-2-piperazinyl-6-chloro-1,2,3,4-tetrahydronaphthalene or a pharmaceutically acceptable acid addition salt thereof.

* * * * *

UNITED STATES PATENT AND TRADEMARK OFFICE
CERTIFICATE OF CORRECTION

PATENT NO. : 5,026,707

DATED : June 25, 1991

INVENTOR(S) : James A. Nixon, Richard P. Pioch, John M. Schaus, Robert D. Titus

It is certified that error appears in the above-identified patent and that said Letters Patent is hereby corrected as shown below:

Claim 1, Column 39, line 67, delete "pharmaceutically acceptable acid addition salts", and insert therefor -- a pharmaceutically acceptable acid addition salt --.

Claim 3, Column 40, line 6, before "thioalkyl", insert -- $C_1-C_3$ --.

Claim 12, Column 40, line 18, delete "Claim 1", and insert therefor -- Claim 7 --.

Claim 21, Column 40, line 65, delete "$R_2$" (first instance), and insert therefor -- $R_5$ --.

Claim 25, Column 41, line 68, before the word "and" insert -- $C_1-C_3$ alkyl --.

Claim 25, Column 42, line 4, before "thioalkyl", insert -- $C_1-C_3$ --.

Claim 25, Column 42, line 9, after "cyano", insert -- all subject to the following provisos: --.

Claim 27, Column 42, line 55, delete "R", and insert therefor -- $R_1$ --.

Claim 30, Column 43, line 40, delete "1-methYl", and insert therefor -- 1-methyl --.

Claim 31, Column 44, line 7, delete "$C_1C_3$", and insert therefor -- $C_1-C_3$ --.

UNITED STATES PATENT AND TRADEMARK OFFICE
CERTIFICATE OF CORRECTION

PATENT NO. : 5,026,707

DATED : June 25, 1991

INVENTOR(S) : James A. Nixon, Richard P. Pioch, John M. Schaus, Robert D. Titus.

It is certified that error appears in the above-identified patent and that said Letters Patent is hereby corrected as shown below:

Claim 33, Column 44, line 41, delete "$C_1$-$C_3$ a alkoxy, $C_1$-$C_3$ thioalkyl, alkyl", and insert therefor -- $C_1$-$C_3$ alkoxy, $C_1$-$C_3$ thioalkyl, $C_1$-$C_3$ alkyl --.

Claim 35, Column 46, line 1, after "hydrogen", insert -- and halo; $R^4$ is selected from the group consisting of hydrogen, --.

Claim 35, Column 46, line 5, delete "$C_1$-$C_3$ a alkyl", and insert therefor -- $C_1$-$C_3$ alkyl --.

Signed and Sealed this

Eleventh Day of May, 1993

Attest:

MICHAEL K. KIRK

*Attesting Officer*    *Acting Commissioner of Patents and Trademarks*